(12) United States Patent
Lelkes et al.

(10) Patent No.: US 9,725,693 B2
(45) Date of Patent: Aug. 8, 2017

(54) THREE-DIMENSIONAL SCAFFOLDS FOR TISSUE ENGINEERING MADE BY PROCESSING COMPLEX EXTRACTS OF NATURAL EXTRACELLULAR MATRICES

(71) Applicant: Drexel University, Philadelphia, PA (US)

(72) Inventors: Peter I. Lelkes, Cherry Hill, NJ (US); Mengyan Li, Philadelphia, PA (US); Anat Perets, Narberth, PA (US); Honesto Poblete, Philadelphia, PA (US); Philip Lazarovici, Jerusalem (IL)

(73) Assignee: Drexel University, Philadelphia, PA (US)

(*) Notice: Subject to any disclaimer, the term of this patent is extended or adjusted under 35 U.S.C. 154(b) by 41 days.

(21) Appl. No.: 14/546,534

(22) Filed: Nov. 18, 2014

(65) Prior Publication Data
US 2015/0079143 A1    Mar. 19, 2015

Related U.S. Application Data

(62) Division of application No. 11/917,644, filed as application No. PCT/US2006/023813 on Jun. 19, 2006, now Pat. No. 8,932,620.

(60) Provisional application No. 60/691,612, filed on Jun. 17, 2005.

(51) Int. Cl.
| | | |
|---|---|---|
| *A61F 2/00* | (2006.01) | |
| *C12N 5/00* | (2006.01) | |
| *A61K 35/12* | (2015.01) | |
| *A61L 27/36* | (2006.01) | |
| *A61L 27/38* | (2006.01) | |
| *A61L 27/56* | (2006.01) | |
| *A61K 35/30* | (2015.01) | |
| *A61K 38/39* | (2006.01) | |
| *C12N 5/071* | (2010.01) | |

(52) U.S. Cl.
CPC ........... *C12N 5/0062* (2013.01); *A61K 35/12* (2013.01); *A61K 35/30* (2013.01); *A61K 38/39* (2013.01); *A61L 27/3633* (2013.01); *A61L 27/3675* (2013.01); *A61L 27/3683* (2013.01); *A61L 27/38* (2013.01); *A61L 27/56* (2013.01); *C12N 5/0068* (2013.01); *C12N 5/0686* (2013.01); *C12N 2533/90* (2013.01)

(58) Field of Classification Search
None
See application file for complete search history.

(56) References Cited

U.S. PATENT DOCUMENTS

| | | | |
|---|---|---|---|
| 4,829,000 | A | 5/1989 | Kleinman et al. |
| 6,146,892 | A | 11/2000 | Ma et al. |
| 6,225,122 | B1 | 5/2001 | Sah et al. |
| 6,337,198 | B1 | 1/2002 | Levene et al. |
| 6,482,231 | B1 | 11/2002 | Abatangelo et al. |
| 6,790,455 | B2 | 9/2004 | Kim et al. |
| 2003/0158607 | A1 | 8/2003 | Carr, Jr. et al. |
| 2004/0037813 | A1 | 2/2004 | Simpson et al. |
| 2004/0166169 | A1 | 8/2004 | Malaviya et al. |

OTHER PUBLICATIONS

Kim et al., International Journal of Biological macromolecules, available online Jun. 6, 2005, vol. 36, p. 54-60.*
Kang et al., Biomaterials, 1999, vol. 20, p. 1339-1344.*
Tang et al., Pharmaceutical Research, 2004, vol. 21, No. 2, p. 191-200.*
Lutolf et al., Nature Biotechnology, Jan. 2005, vol. 23, No. 1, p. 47-55.*
Silva et al., Science, 2004, vol. 303, p. 1352-1355.*
PCT International Search Report and Written Opinion for PCT/US2006/023813 issued Feb. 12, 2007.

* cited by examiner

*Primary Examiner* — Kade Ariani
(74) *Attorney, Agent, or Firm* — Saul Ewing LLP; Kathryn Doyle

(57) ABSTRACT

Methods of making a biologically active three-dimensional scaffold capable of supporting growth and differentiation of a cell are described. Biologically active three-dimensional scaffold made by the methods of the invention and an engineered tissue made from the scaffolds are described. Fibers of desired porosity can be obtained from non-structural ECM by lyophilization and/or electrospinning which can be useful for numerous tissue engineering applications requiring complex scaffolds, such as wound healing, artificial skin (burns), soft tissue replacement/repair and spinal cord injury.

4 Claims, 26 Drawing Sheets

THREE-DIMENSIONAL SCAFFOLDS FOR TISSUE ENGINEERING MADE BY PROCESSING COMPLEX EXTRACTS OF NATURAL EXTRACELLULAR MATRICES

CROSS-REFERENCE TO RELATED APPLICATION

The present application is a divisional application of, and claims priority to U.S. patent application Ser. No. 11/917,644, filed Dec. 14, 2007, now allowed, which is a 35 U.S.C. §371 national phase application of, and claims priority to, International Application No. PCT/US2006/023813, filed Jun. 19, 2006, which claims priority under 35 U.S.C. §119 (e) to U.S. Provisional Application No. 60/691,612, filed Jun. 17, 2005, all of which are hereby incorporated by reference in their entireties herein.

BACKGROUND OF THE INVENTION

1. Field of Invention

This invention relates to three dimensional nanofibrous scaffolds made from complex extracellular matrix (ECM) for tissue engineering applications.

2. Description of Related Art

Tissue engineering is a multidisciplinary field that involves the development of biological substitutes that restore, maintain or improve tissue functions. This field has the potential of overcoming the limitations of conventional treatments by producing a supply of organ and tissue substitutes biologically tailored to a patient. There is a continuing need in biomedical sciences for scaffolds of biocompatible compositions and of nanofibrous structure which closely mimic the composition and structure of natural ECM and which can be used in manufacturing devices for implantation within or upon the body of an organism.

Several techniques have been developed to produce tissue engineering scaffolds from biodegradable and bioresorbable polymers. For synthetic polymers, these are usually based on solvent casting-particulate leaching, phase separation, gas foaming and fibre meshes. For natural collagen scaffolds, these can be made by freezing a dispersion/solution of collagen and then freeze-drying it. Freezing the dispersion/solution results in the production of ice crystals that grow and force the collagen into the interstitial spaces, thus aggregating the collagen. The ice crystals are removed by freeze-drying which involves inducing the sublimation of the ice and this gives rise to pore formation; therefore the water passes from a solid phase directly to a gaseous phase and eliminates any surface tension forces that can collapse the delicate porous structure.

A major challenge for tissue engineering is to generate scaffolds which are sufficiently complex in mimicking the functions of the extracellular matrix (ECM) and yet not immunogenic. Different approaches to making tissue scaffolds have been described by Radisic et al., High-density seeding of myocyte cells for cardiac tissue engineering. Biotechnol Bioeng. 2003 May 20; 82(4):403-14; Boland et al., Electrospinning collagen and elastin: preliminary vascular tissue engineering. Front Biosci. 2004 May 1; 9:1422-32; Matthews et al., Electrospinning of collagen nanofibers. Biomacromolecules. 2002 March-April; 3(2):232-8; Huang et al., Engineered collagen-PEO nanofibers and fabrics. J Biomater Sci Polym Ed. 2001; 12(9):979-93.

However, complex ECM extracts, such as MATRIGEL and others, such as DECM from the submucosa of porcine small intestine (SIS, Hodde J P, Record R D, Liang H A, Badylak S F. Vascular endothelial growth factor in porcine-derived extracellular matrix. Endothelium. 2001; 8(1):11-24) or from the cornea (Desgranges P, Tardieu M, Loisance D, Barritault D. Extracellular matrix covered biomaterials for human endothelial cell growth (see Int J Artif Organs. 1992 December; 15(12):722-6) contain numerous differentiative cues which are not present in synthetic scaffolds or lost through conventional scaffold preparation techniques.

Other sources of ECM known to be effective for tissue remodeling include but are not limited to small intestine submucosa, stomach, bladder, alimentary, respiratory, or genital submucosa, or liver basement membrane. See, e.g., U.S. Pat. Nos. 6,379,710, 6,171,344; 6,099,567; and 5,554,389.

U.S. Pat. No. 5,939,323 to Valentini et al. describes hyaluronic acid derivitized scaffolds made by lyophilization. It was found that freeze/drying and air drying techniques did not yield interconnecting pores while lyophilizing from the wet state yielded scaffolds with interconnecting pores.

U.S. Pat. No. 6,787,357 to Bowlin et al. and US2004/022933A1 to Bowlin et al. disclosed the use of fibrin as ECM in forming an engineered tissue by electrospinning.

U.S. Patent Application Publication No. 2004/0191215A1 to Froix et al. disclosed compositions for initiating and promoting repair and regeneration of tissue.

U.S. Patent Application Publication No. 2004/0037813A1 to Simpson et al. described methods of making electroprocessed collagen and using the electroprocessed collagen in preparation of engineered tissue. Simpson et al. teach isolating collagen from tissue prior to electroprocessing or combining the isolated collagen with other proteins and substances to mimic ECM.

U.S. Pat. No. 6,398,819 to Bell described using animal tissues as starting materials for producing extracellular matrix particulates by a freeze drying process. The matrix particulates were then applied to collagen scaffolds, which can be seeded with living cells or the particulates may alone be seeded with living cells. This patent does not describe obtaining extracts of extracellular matrix or making scaffolds therefrom.

U.S. Patent Application Publication No. 20040166169A1 to Malaviya et al. described a method of making an implantable scaffold for repairing damaged or diseased tissue. The method includes the step of suspending, mixing, or otherwise placing pieces of a naturally occurring extracellular matrix material in a liquid. The naturally occurring extracellular matrix material and the liquid are formed into a mass. The liquid is subsequently driven off so as to form interstices in the mass. This patent does not describe obtaining extracts of extracellular matrix.

US2004/0258729A1 to Czernuszka et al. described a process for preparing a scaffold of polymer, generally a biocompatible polymer, ideally biodegradable or bioresorbable in nature for tissue engineering purposes, which comprises placing a composition comprising the polymer in mould possessing one or more voids therein, said mould being a negative of the desired shape of the scaffold, causing the polymer to acquire the shape of the mould, removing the mould and causing pores to be formed in the polymer, and without affecting the polymer. Czernuszka et al. do not describe making nanofibrous scaffolds from unfractionated ECM extracts.

A PCT Patent Application Publication No. WO05121316A by Bortolotto et al. disclosed a composition of matter useful in promoting cell growth including differentiation, proliferation, division and/or morphological changes in a cell or tissue, said composition comprising either a cell-based or cell-free extract of a muscle tissue preparation which preparation provides a source of, but not limited to, laminin, collagen I, collagen IV, entactin/nidogen, heparan sulfate proteoglycan as well as other components including cytokines and growth factors such as, but not limited to, one or more of EGF, bFGF, NGF, PDGF, IGF-1, TGF-B, VEGF and TNF-a or homologs thereof.

Attempts to make scaffolds suitable for tissue engineering applications mostly focus on mimicking the extracellular matrix by adding various individual components to the isolated collagen. It is known that intracellular matrix derived from different tissues varies in its composition and structure. Thus, reconstituting naturally occurring matrix is a formidable task Basement membranes are thin, but continuous sheets that separate epithelium from stroma and surround nerves, muscle fibers, smooth muscle cells and fat cells. Basement membranes comprise type IV collagen, the glycoproteins laminin, entactin, nidogen and heparan sulfate proteoglycans. Various components of the basement membrane are known to interact with each other. In vitro studies with purified components show that laminin binds through its short chains to native but not to denatured type IV collagen and through a domain in its long chain to the heparan sulfate proteoglycan. Each of these basement membrane components is soluble. However, when these macromolecules are mixed together in vitro, they form a floccular precipitate containing laminin to type IV collagen to heparan sulfate proteoglycan in a 1:1:0.1 molar ratio. However, this precipitate lacks the resiliency and consistency expected of basement membranous structures. Purified components of basement membrane have been used previously as a coating for cultured cells. However, such material was soluble and did not form a three dimensional matrix.

U.S. Pat. No. 4,829,000 to Kleinman et al. disclosed making reconstituted basement membrane composition with biological activity capable of forming a three dimensional hydrogel matrix. The major components of the composition include laminin, type IV collagen, heparin sulfate proteoglycan, entactin and nidogen. It was shown that this composition can support cell adhesion, growth and differentiation beyond that known for the individual components. However, the three dimensional matrix described in this patent is a gel only. This patent does not describe making a fibrous structure or a scaffold mimicking the structure of extracellular matrix and therefore cannot be used as a scaffold for tissue engineering applications in its current form.

Therefore, despite the foregoing developments, there is a need in the art for fibrous or porous scaffolds for tissue engineering applications which can support growth and differentiation of cells.

All references cited in this disclosure are incorporated herein by reference in their entireties.

BRIEF SUMMARY OF THE INVENTION

The objective of this invention is to leverage techniques such as electrospinning and/or lyophilization and critical point drying for creating 3-D fibrous and microporous scaffolds that retain the complexity of the ingredients and functionality of natural ECM. As an example, the extracted ECM from murine EHS tumor (the commercial analog is sold as MATRIGEL (BD Biosciences, San Jose, Calif.) was processed into fibers and scaffolds. A lyophilized ECM extract (ECME) was used either directly as a porous scaffold or further processed by electrospinning to yield nanofiburos scaffolds. Both these products contain all proteins and growth factors necessary for tissue-specific cell proliferation and differentiation. Both electrospun and lyophilized scaffolds are suitable for tissue engineering purposes, such as, for example, would healing, artificial skin, spinal cord injury, etc. If extracted from the patients' own tissues, these scaffolds will be useful as autologous scaffolds thus avoiding immune complications.

These ECM-based processed scaffolds retain the complex protein mixture present in the original ECM. Hence, these scaffolds retain functional cues necessary for organotypic differentiation of the target tissues. Furthermore, these scaffolds alone or in combination with other (synthetic) polymers provide good mechanical properties which facilitate cell penetration and proliferation within the scaffolds. Finally, the complex protein mix in these scaffolds contains also bioactive growth/differentiation factors, which provide nutrition to support cell growth even without serum. Thus, inventors have discovered that scaffolds of the invention can act locally as biomimetics facilitating, for example, tissue repair without additional inclusion of exogenous growth/differentiation factors or cells.

Unfractionated ECM extracts as used in this invention represent complex mixtures of biologically-derived extracellular matrix proteins, specifically of basement membrane proteins. A non-limiting example of a complex ECM extract is MATRIGEL. MATRIGEL, an extracellular matrix (ECM) isolated from the murine Engelbreth-Holm-Swarm (EHS) sarcoma, is a complex mixture of basement membrane proteins. Unlike artificial synthetic scaffolds, MATRIGEL provides a natural, biocompatible environment to cells. MATRIGEL is liquid at 4° C. but forms a semi-solid, viscous hydrogel at 37° C. Thus, in its present incarnation, it is not very useful as a scaffold for tissue engineering purposes. Inventors have discovered that processing MATRIGEL will enhance its inherent value as a biocompatible scaffold biomaterial. Inventors generated functional 3-D biologically active scaffold with microporous and fibrous structures using lyophilization, electrospinning and critical point drying (CPD). The MATRIGEL fibers produced by CPD were very small (50-60 nm), while electrospinning yielded larger fibers (~1 µm in diameter). Using electrospinning, aligned fibrous scaffolds were generated which will be of advantage for generation tissues with aligned architecture, including but not limited to cardiac tissues and for guiding axonal growth.

Biologically active scaffolds obtained by lyophylization were highly porous (>80%), a property that helps to accommodate cells and direct cell growth and tissue regeneration. The pore size (~20 µm) of the lyophilized biologically active scaffolds may allow for the formation of blood vessels and tissue. The ability of a neural PC12 cell model to populate the engineered scaffolds and to undergo neuronal differentiation was demonstrated. The biologically active scaffolds of the invention represent a promising novel approach towards neuronal tissue engineering, e.g., for treating spinal cord injury. Also, the ability of cardiac myoblast cells H9C2 to differentiate was demonstrated.

Uniqueness and non-obviousness of this invention is the combination of using ECM and post-processing techniques of lyophilization, CPD, and electrospinning. What has been electrospun so far in prior art is mainly collagen type I, which is a "structural" Extracellular Matrix (ECM) molecule. By contrast, MATRIGEL is a very complex mixture of non-structural ECM molecules (such as collagen IV and laminin). In addition, and what makes it unique, MATRIGEL contains a plethora of growth factors and other biologically active molecules. It was doubted previously whether the biological activity of these molecules could be retained. This invention demonstrates that it is retained after processing (e.g., electrospinning).

Inventors have discovered that scaffolds or fibers of desired porosity can be obtained from non-structural ECM extracts by lyophilization, CPD and/or electrospinning.

This invention is useful for numerous tissue engineering applications requiring complex scaffolds, such as wound healing, artificial skin (burns), soft tissue replacement/repair, spinal cord injury, etc.

Accordingly, the present invention relates to an electroprocessing method of making a biologically active three-dimensional scaffold capable of supporting growth and differentiation of a cell, the method comprising: providing an unfractionated extracellular matrix extract from a mammalian tissue; freezing the unfractionated aqueous extracellular matrix extract at a temperature of at most −60° C. and freeze drying under a negative pressure to provide a lyophilized unfractionated extracellular matrix extract; combining the lyophilized unfractionated extracellular matrix extract with an aqueous or non-aqueous solvent to form a solution, a hydrogel or a suspension; electroprocessing the lyophilized unfractionated extracellular matrix extract in a form of a solution, a hydrogel or a suspension and thereby making the biologically active three-dimensional scaffold comprising at least one of fibers or droplets.

In certain embodiments of the electroprocessing method, the unfractionated extracellular matrix extract is provided in an aqueous medium.

In certain embodiments of the electroprocessing method, said freezing the unfractionated aqueous extracellular matrix extract is conducted at a temperature of from −80° C. to −130° C.

In certain embodiments of the electroprocessing method, the method further comprises electroprocessing the lyophilized unfractionated extracellular matrix extract into a mold.

In certain embodiments of the electroprocessing method, the method further comprises crosslinking the lyophilized unfractionated extracellular matrix extract subsequent to said electroprocessing, wherein the lyophilized unfractionated extracellular matrix extract is contacted with a crosslinker.

In certain embodiments, electroprocessing is at least one of electrospinning, electrospraying, electroaerosoling, or electrosputtering. In a preferred embodiment, electroprocessing is electrospinning.

In certain embodiments of the electroprocessing method, the unfractionated extracellular matrix extract is derived from a basement membrane.

In certain embodiments of the electroprocessing method, the unfractionated extracellular matrix extract comprises about 60-85% laminin, 5-30% collagen IV, 1-10% nidogen, 1-10% heparan sulfate proteoglycan and 1-5% entactin by weight.

In certain embodiments of the electroprocessing method, the unfractionated extracellular matrix extract comprises less than 50% collagen I, collagen II or collagen III cumulatively or singly.

In certain embodiments of the electroprocessing method, the biologically active three dimensional scaffold consists essentially of 60-85% laminin, 5-30% collagen IV, 1-10% nidogen, 1-10% heparan sulfate proteoglycan and 1-5% entactin by weight.

In certain embodiments of the electroprocessing method, the unfractionated extracellular matrix extract further comprises an additional substance. In certain embodiments, the additional substance is at least one of a cell, a pharmaceutical agent, an imaging agent, a biologically active agent and a polymer.

In certain embodiments of the electroprocessing method, the basement membrane is derived from at least one of an Engelberth-Holm-Swarm tumor, human placenta, mammalian Decemet's membrane, mammalian kidney epithelium, and mammalian small intestinal submucosa.

In another aspect, the invention relates to a biologically active three-dimensional scaffold made by the electroprocessing method. In certain embodiments, the biologically active three-dimensional scaffold includes fibers or droplets which have an average diameter of between about 30 nm and about 1 μm. In certain embodiments, the unfractionated extracellular matrix extract comprises about 60-85% laminin, 5-30% collagen IV, 1-10% nidogen, 1-10% heparan sulfate proteoglycan and 1-5% entactin by weight. In certain embodiments, the unfractionated extracellular matrix extract comprises less than 50% collagen I, collagen II or collagen III cumulatively or singly. In certain embodiments, the unfractionated extracellular matrix extract consists essentially of 60-85% laminin, 5-30% collagen IV, 1-10% nidogen, 1-10% heparan sulfate proteoglycan and 1-5% entactin by weight.

In another aspect, the invention relates to an engineered tissue made by contacting the biologically active three-dimensional scaffold made by the electroprocessing method with cells in vivo or in vitro under conditions effective to allow interaction between the biologically active three-dimensional scaffold and the cells. In certain embodiments, the cells are members selected from the group consisting of stem cells, progenitor cells, and differentiated cells. In certain embodiments, the cells are at least one of neural cells, epithelial cells, cardiac myocytes, pulmonary lung cells, keratinocytes, endothelial cells. In certain embodiments, the cells are PC12 or neuronal-restricted precursor (NRP) cells and the engineered tissue is a neurone producing tissue.

In certain embodiments, the unfractionated extracellular matrix extract comprises about 60-85% laminin, 5-30% collagen IV, 1-10% nidogen, 1-10% heparan sulfate proteoglycan and 1-5% entactin by weight. In certain embodiments, the unfractionated extracellular matrix extract comprises less than 50% collagen I, collagen II or collagen II cumulatively or singly. In certain embodiments, the unfractionated extracellular matrix extract consists essentially of 60-85% laminin, 5-30% collagen IV, 1-10% nidogen, 1-10% heparan sulfate proteoglycan and 1-5% entactin by weight. In certain embodiments, the engineered tissue further comprising an additional substance. Non-limiting examples of such substances include a cell, a pharmaceutical agent, an imaging agent, a biologically active agent and a polymer.

In yet another aspect, the invention relates to a lyophilization method of making a biologically active three-dimensional scaffold capable of supporting growth and differentiation of a cell, the method comprising: providing an unfractionated extracellular matrix extract from a mammalian tissue in a form of a powder, a solution, a hydrogel or a suspension; placing the unfractionated extracellular matrix extract in a mold; freezing the unfractionated extra cellular matrix extract at 0° C. or below at a controlled freezing rate; freeze-drying the unfractionated extra cellular matrix extract by subjecting the unfractionated extracellular matrix extract to a temperature of at most −60° C. for a time sufficient to remove at least 90% of a liquid from the unfractionated extracellular matrix extract and thereby obtaining a lyophilized unfractionated extracellular matrix extract; and optionally crosslinking the lyophilized unfractionated extracellular matrix extract by contacting with a crosslinker and thereby providing the biologically active three-dimensional scaffold having porous morphology.

In certain embodiments of the method, freeze-drying is conducted at a temperature of between about −130° C. to about −80° C. In certain embodiments of the method, the unfractionated extracellular matrix extract is provided in an organic solvent. In certain embodiments of the method, the unfractionated extracellular matrix extract is provided in an aqueous medium. In certain embodiments, the method further comprises crosslinking the lyophilized unfractionated extracellular matrix extract by contacting with a crosslinker.

In yet another aspect, the invention relates to a biologically active three-dimensional scaffold made by the lyophilization method. In certain embodiments, the pores have an average diameter of between about 10 µm and about 200 µm. In certain embodiments, the average diameter of pores is between about 50 µm and about 120 µm.

In certain embodiments, at least 45% of the biologically active three dimensional scaffold comprise pores. In certain embodiments, at most 95% of the biologically active three dimensional scaffold comprise pores. In certain embodiments, pores constitute 75% to 85%. In certain embodiments, the matrix comprises pores having an average area of between about 10 square µm and 200 square µm.

In yet another aspect, the invention relates to an engineered tissue made by contacting the biologically active three dimensional scaffold made by the lyophilization method with cells in vivo or in vitro under conditions effective to allow interaction between the biologically active three dimensional scaffold and the cells. In certain embodiments, the cells are members selected from the group consisting of stem cells, progenitor cells, and differentiated cells. In certain embodiments, the cells are at least one of neural cells, epithelial cells, cardiac myocytes, pulmonary lung cells, keratinocytes, endothelial cells. In certain embodiments, the cells are PC12 or neuronal-restricted precursor (NRP) cells and the engineered tissue is a neurone producing tissue.

In certain embodiments, the unfractionated extracellular matrix extract comprises about 60-85% laminin, 5-30% collagen IV, 1-10% nidogen, 1-10% heparan sulfate proteoglycan and 1-5% entactin by weight. In certain embodiments, the unfractionated extracellular matrix extract comprises less than 50% collagen I, collagen II or collagen III cumulatively or singly.

In certain embodiments, the unfractionated extracellular matrix extract consists essentially of 60-85% laminin, 5-30% collagen IV, 1-10% nidogen, 1-10% heparan sulfate proteoglycan and 1-5% entactin by weight. In certain embodiments, the tissue further comprises an additional substance. In certain embodiments, the additional substance is at least one of a cell, a pharmaceutical agent, an imaging agent, a biologically active agent and a polymer.

In yet another aspect, the invention relates to a critical point drying method of making a nanofibrous biologically active three-dimensional scaffold capable of supporting growth and differentiation of a cell, the method comprising: providing an unfractionated extracellular matrix extract of a mammal in a form of a powder, a solution, a hydrogel or a suspension; placing the unfractionated extracellular matrix extract in a mold; crosslinking the unfractionated extracellular matrix extract by contacting with a crosslinker to form a crosslinked unfractionated extracellular matrix extract; contacting the crosslinked unfractionated extracellular matrix extract with a dehydrating substance (e.g., ethanol) to the crosslinked unfractionated extracellular matrix extract to form a dehydrated unfractionated extracellular matrix extract; critical point drying the dehydrated unfractionated extracellular matrix extract with a transitional media to obtain the nanofibrous biologically active three-dimensional scaffold. In certain embodiments, the unfractionated extracellular matrix extract is provided in an aqueous medium. In certain embodiments, said contacting comprises sequentially contacting with graded ethanol. In certain embodiments, the transitional media comprises liquid carbon dioxide.

In certain embodiments, the nanofibrous biologically active three-dimensional scaffold is made of fibers having diameter between 30 and 80 nm.

In yet another aspect, the invention relates to a nanofibrous biologically active three-dimensional scaffold made by the critical point drying method. In certain embodiments, the unfractionated extracellular matrix extract comprises about 60-85% laminin, 5-30% collagen IV, 1-10% nidogen, 1-10% heparan sulfate proteoglycan and 1-5% entactin by weight. In certain embodiments, the unfractionated extracellular matrix extract comprises less than 50% collagen I, collagen II or collagen III cumulatively or singly. In certain embodiments, the unfractionated extracellular matrix extract consists essentially of 60-85% laminin, 5-30% collagen IV, 1-10% nidogen, 1-10% heparan sulfate proteoglycan and 1-5% entactin by weight.

In yet another aspect, the invention relates to an engineered tissue made by contacting the nanofibrous biologically active three-dimensional scaffold made by the critical point drying method with cells in vivo or in vitro under conditions effective to allow interaction between the nanofibrous biologically active three-dimensional scaffold and the cells. In certain embodiments, the cells are members selected from the group consisting of stem cells, progenitor cells, and differentiated cells. In certain embodiments, the cells are at least one of neural cells, epithelial cells, cardiac myocytes, pulmonary lung cells, keratinocytes, and endothelial cells. In certain embodiments, the cells are PC12 or neuronal-restricted precursor (NRP) cells and the engineered tissue is a neurone producing tissue. In certain embodiments, the unfractionated extracellular matrix extract comprises about 60-85% laminin, 5-30% collagen IV, 1-10% nidogen, 1-10% heparan sulfate proteoglycan and 1-5% entactin by weight. In certain embodiments, the unfractionated extracellular matrix extract comprises less than 50% collagen I, collagen II or collagen III cumulatively or singly. In certain embodiments, the unfractionated extracellular matrix extract consists essentially of 60-85% laminin, 5-30% collagen IV, 1-10% nidogen, 1-10% heparan sulfate proteoglycan and 1-5% entactin by weight. In certain embodiments, the engineered tissue further comprising an additional substance as described above.

In yet another aspect, the invention relates to a use of the engineered tissue made by the above described methods for brain or spinal cord tissue repair or regeneration.

In yet another aspect, the invention relates to a method of use the engineered tissue of the invention made by the above described methods for brain or spinal cord tissue repair or regeneration, the method comprises administering the engineered tissue of the invention to a mammal in need of said brain or spinal cord tissue repair or regeneration.

BRIEF DESCRIPTION OF SEVERAL VIEWS OF THE DRAWINGS

The invention will be described in conjunction with the following drawings in which like reference numerals designate like elements and wherein.

DETAILED DESCRIPTION OF PREFERRED EMBODIMENTS OF THE INVENTION

Figure 1A:
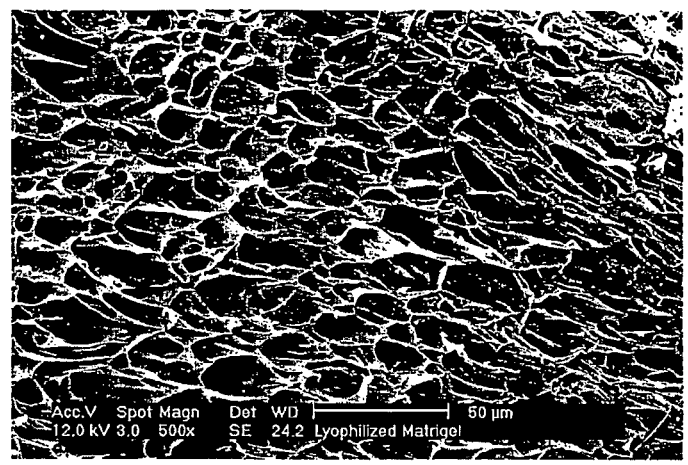
FIGS. 1A-C are scanning electron microscope (SEM) pictures of lyophilized MATRIGEL in a tube.

The invention involves three-dimensional biodegradable scaffolds comprising an unfractionated extract from natural extracellular matrix (ECM) which is processed into fibers or droplets by lyophilization, electroprocessing, a critical point drying process or a combination of these processes. Unexpectedly, the inventors have discovered that despite the common belief, the bioactivity of extracellular matrix (ECM) biomolecules was not lost during these processes due to the solubilization in organic solvents of subjecting to processing conditions. The scaffolds of the invention derived from an unfractionated extracellular matrix extract retain functional cues necessary for cell growth and proliferation. Furthermore, these scaffolds can be further modified by incorporate other proteins and growth factors facilitating cell attachment, proliferation, and differentiation within the scaffolds.

The scaffolds of the invention can be used for tissue engineering, reconstruction and repair. Exemplary applications include wound healing, artificial skin (e.g., for burns), (soft) tissue replacement/repair, spinal cord injury, etc.

The porous scaffold has interconnected pores that permit cells to grow into the scaffold, preferably completely penetrating the scaffold with cells, and thereby, eventually replacing the scaffold with tissue. The scaffold can be fabricated to be virtually any shape, size or thickness, and can be produced to various porosities and pore sizes, depending upon the application. The scaffold is biodegradable, so that eventually it can be completely replaced by tissue. The scaffold degrades slowly in concert with new tissue formation. Such a scaffold offers the advantage of promoting host cells to migrate, adhere, proliferate and synthesize new tissue inside the pores.

Void volumes for the scaffold according to the invention can range from 40-90%. Pore sizes for the scaffold of the invention can range from 10-200 micrometers.

ECM is a complex network of secreted extracellular molecules. ECM main components are various glycoproteins and glycosaminoglycans (GAG) (e.g., proteoglycans and hyaluronic acid). In most animals, the most abundant glycoproteins in the ECM are collagens. ECM also contains many other components: proteins such as fibrin, elastin, fibronectins, laminins, and nidogens, and minerals such as hydroxyapatite, or fluids such as blood plasma or serum with secreted free flowing antigens. In addition it sequesters a wide range of cellular growth factors.

Due to this diversity, ECM can serve many functions, such as providing support and anchorage for cells, providing a way of separating the tissues, and regulating intercellular communication. The ECM regulates a cell's dynamic behavior.

In a preferred embodiment, ECM is a reconstituted, basement-membrane-derived extracellular composition (MATRIGEL) which polymerizes on heating and promotes cell growth and differentiation in vitro and in vivo. MATRIGEL is described by U.S. Pat. No. 4,829,000 to Kleinman et al.

The reconstituted matrix (MATRIGEL) is known to promote the growth and tissue-specific morphogenesis and differentiation of a variety of cells. In particular, the reconstituted basement membrane gel is an excellent substrate for (e.g., lung and kidney epithelia cells) in culture. MATRI- GEL has also been demonstrated to promote cell adhesion, growth and differentiation of a multiplicity of cells including neurons, hepatocytes, sertoli cells, hair follicles, thyroid cells and the like. In addition, sertoli cells cultured within the gel have been subsequently transplanted back into the animal with good survival and maturation of the spermatids. The composition of the present invention has also been found to promote nerve regeneration (optic and sciatic) in vivo and allows for organ reconstitution as well.

In certain embodiments, the basement-membrane-derived composition comprises a biologically active polymerizable extract containing in parts by weight about 60-85% laminin, 5-30% collagen IV, 1-10% nidogen, 1-10% heparan sulfate proteoglycan and 1-5% entactin.

In certain embodiments, the basement-membrane-derived composition is derived from Engelbreth-Holm-Swarm tumor (EHS). Preparation of EHS Tumor Extract is described in Example 1.

In certain embodiments, the basement-membrane-derived composition is derived from human placenta. Preparing MATRIGEL using an extract from human placenta also reduces the possibility of immunological interaction or rejection when such MATRIGEL is used in humans. Human placental preparation of basement membrane MATRIGEL is described in Example 2.

In another aspect of the invention, lyophilized and reconstituted hydrogels generated in orienting electrical/magnetic fields can be used to create oriented biologically active scaffolds using techniques known to those skilled in the art.

DEFINITIONS

The term "biologically active" as used herein means capable of supporting normal growth and histiotypic differentiation of various cell types when cultured including but not limited to stem cells, progenitor cells, endothelial cells, epithelial cells (e.g., lung and kidney) and preferably, neuronal cells.

The terms "electroprocessing" and "electrodeposition" shall be defined broadly to include all methods of electrospinning, electrospraying, electroaerosoling, and electrosputtering of materials, combinations of two or more such methods, and any other method wherein materials are streamed, sprayed, sputtered or dripped across an electric field and toward a target. The electroprocessed material can be electroprocessed from one or more grounded reservoirs in the direction of a charged substrate or from charged reservoirs toward a grounded target. "Electrospinning" means a process in which fibers are formed from a solution or melt by streaming an electrically charged solution or melt through an orifice. "Electroaerosoling" means a process in which droplets are formed from a solution or melt by streaming an electrically charged polymer solution or melt through an orifice. The term electroprocessing is not limited to the specific examples set forth herein, and it includes any means of using an electrical field for depositing a material on a target.

The electroprocessed ECM extract may be made using any electroprocessing technique, including, but not limited to, electrospinning, electroaerosol, electrospraying or electrosputtering techniques, or any combination thereof. Accordingly, electroprocessed droplets, particles, fibers, fibrils, or combinations thereof are all included in the electroprocessed ECM extract compositions of the present invention. In a preferred embodiment, ECM extract is frozen, lyophilized and then electrospun to form the biologically active scaffold.

The term "biologically active scaffold" as used herein means a scaffold capable of supporting growth and histiotypic differentiation of a cell.

The term "unfractionated extracellular matrix extract" as used herein denotes an extract obtained without fractionation into separate proteins from a tissue specific naturally occurring extracellular matrix of a mammal.

The term "electroprocessing" or "electrodeposition" as used herein includes all methods of electrospinning, electrospraying, electroaerosoling, and electrosputtering of materials, combinations of two or more such methods, and any other method wherein materials are streamed, sprayed, sputtered or dripped across an electric field and toward a target. The electroprocessed material can be electroprocessed from one or more grounded reservoirs in the direction of a charged substrate or from charged reservoirs toward a grounded target. "Electrospinning" means a process in which fibers are formed from a solution or melt by streaming an electrically charged solution or melt through an orifice. "Electroaerosoling" means a process in which droplets are formed from a solution or melt by streaming an electrically charged polymer solution or melt through an orifice. The term electroprocessing is not limited to the specific examples set forth herein, and it includes any means of using an electrical field for depositing a material on a target.

Throughout this application the term "solution" is used to describe the liquid in the reservoirs of the electroprocessing method. The term is defined broadly to include any liquids that contain materials to be electroprocessed. It is to be understood that any solutions capable of forming a material during electroprocessing are included within the scope of the present invention. In this application, the term "solution" also refers to suspensions or emulsions containing the material or anything to be electrodeposited. "Solutions" can be in organic or biologically compatible forms. This broad definition is appropriate in view of the large number of solvents or other liquids (polar and non-polar) and carrier molecules, such as poly(ethylene oxide) (PEO), that can be used in the many variations of electroprocessing. In this application, the term "solution" also refers to melts, hydrated gels and suspensions containing the materials, substances or anything to be electrodeposited.

As contemplated in this disclosure, crosslinking can be accomplished by both physical and chemical techniques. Physical crosslinking can be achieved by dehydrothermal treatment and UV or gamma irradiation. Aldehydes such as glutaraldehyde and formaldehyde, polyepoxy resin, acyl azides, carbodiimides and hexamethylene compounds are non-limiting examples of substances for chemical crosslinking.

Also, synthetic materials such as molecules capable of forming some of the named proteins/polypeptides as well as other polymers can be added to the ECM extract during the described processing methods (e.g., electroprocessing) to obtain desired properties.

In certain embodiments, synthetic materials, preferably biologically compatible synthetic materials comprise polymers. Such polymers include but are not limited to the following: poly(urethanes), poly(siloxanes) or silicones, poly(ethylene), poly(vinyl pyrrolidone), poly(2-hydroxy ethyl methacrylate), poly(N-vinyl pyrrolidone), poly(methyl methacrylate), poly(vinyl alcohol), poly(acrylic acid), polyacrylamide, poly(ethylene-co-vinyl acetate), poly(ethylene glycol), poly(methacrylic acid), polylactides (PLA), polyglycolides (PGA), poly(lactide-co-glycolides) (PLGA), polyanhydrides, plyanilines, polypyrroles, and polyorthoesters or any other similar synthetic polymers that may be developed that are biologically compatible.

The term "biologically compatible, synthetic polymers" shall also include copolymers and blends, and any other combinations of the forgoing either together or with other polymers generally. The use of these polymers will depend on given applications and specifications required. A more detailed discussion of these polymers and types of polymers is set forth in Brannon-Peppas, Lisa, "Polymers in Controlled Drug Delivery," Medical Plastics and Biomaterials, November 1997, which is incorporated by reference as if set forth fully herein.

Proteins and peptides associated with membranes are often hydrophobic and thus do not dissolve readily in aqueous solutions. Such proteins can be dissolved in organic solvents such as methanol, chloroform, and trifluoroethanol (TFE) and emulsifying agents. Any other solvents known to one of skill in the protein chemical art may be used, for example solvents useful in chromatography, especially high performance liquid chromatography. Proteins and peptides are also soluble, for example, in HFIP, hexafluoroacetone, chloroalcohols in conjugation with aqueous solutions of mineral acids, dimethylacetamide containing 5% lithium chloride, and in acids such as acetic acid, hydrochloric acid and formic acid. In some embodiments, the acids are very dilute, in others, the acids are concentrated. N-methyl morpholine-N-oxide is another solvent that can be used with many polypeptides. Other examples, used either alone or in combination with organic acids or salts, include the following: triethanolamine; dichloromethane; methylene chloride; 1,4-dioxane; acetonitrile; ethylene glycol; diethylene glycol; ethyl acetate; glycerine; propane-1,3-diol; furan; tetrahydrofuran; indole; piperazine; pyrrole; pyrrolidone; 2-pyrrolidone; pyridine; quinoline; tetrahydroquinoline; pyrazole; and imidazole. Combinations of solvents may also be used.

Substances Combined with Unfractionated Extracellular Matrix Extract and/or Processed Matrix Such as Biologically Active Scaffold In certain embodiments, the unfractionated extracellular matrix extract is combined with one or more substances or additional materials to form an unfractionated extracellular matrix extract composition. The term "substance" in the present invention is used in its broadest definition. In embodiments in which the unfractionated extracellular matrix extract compositions of the present invention comprise one or more substances, substances can include any type or size of molecules, cells, objects or combinations thereof. The compositions of the present invention may comprise one substance or any combination of substances.

In certain embodiments cells are combined with the unfractionated extracellular matrix extract or the biologically active scaffold as an additional substance. Any cell can be used. Some preferred examples include, but are not limited to, stem cells, progenitor cells, committed stem cells, and differentiated cells. Examples of stem cells include, but are not limited to, embryonic stem cells, bone marrow stem cells and umbilical cord stem cells. Other examples of cells used in various embodiments include, but are not limited to, osteoblasts, myoblasts, neuroblasts, fibroblasts, glioblasts, germ cells, hepatocytes, chondrocytes, keratinocytes, smooth muscle cells, cardiac muscle cells, connective tissue cells, glial cells, epithelial cells, endothelial cells, hormone-secreting cells, cells of the immune system, and neurons. In some embodiments it is unnecessary to pre-select the type of stem cell that is to be used, because many types of stem cells can be induced to differentiate in an organ specific pattern once delivered to a given organ. For example, a stem cell delivered to the liver can be induced to become a liver cell simply by placing the stem cell within the liver. Cells in the matrix can serve the purpose of providing scaffolding or seeding, producing certain compounds, or both.

Embodiments in which the additional substance comprises cells include cells that can be cultured in vitro, derived from a natural source, genetically engineered, or produced by any other means. Any natural source of prokaryotic or eukaryotic cells may be used. Embodiments in which the matrix is implanted in an organism can use cells from the recipient, cells from a conspecific donor or a donor from a different species, or bacteria or microbial cells. Cells harvested from a source and cultured prior to use are included.

Some embodiments use cells that have been genetically engineered. The engineering involves programming the cell to express one or more genes, repressing the expression of one or more genes, or both. One example of genetically engineered cells useful in the present invention is a genetically engineered cell that makes and secretes one or more desired molecules. When biologically active scaffolds comprising genetically engineered cells are implanted in an organism, the molecules produced can produce a local effect or a systemic effect, and can include the molecules identified above as possible substances. Cells can also produce antigenic materials in embodiments in which one of the purposes of the matrix is to produce an immune response. Cells may produce substances to aid in the following non-inclusive list of purposes: inhibit or stimulate inflammation; facilitate healing; resist immunorejection; provide hormone replacement; replace neurotransmitters; inhibit or destroy cancer cells; promote cell growth; inhibit or stimulate formation of blood vessels; augment tissue; and to supplement or replace neurons, skin, synovial fluid, tendons, cartilage (including, but not limited to articular cartilage), ligaments, bone, muscle, organs, dura, blood vessels, bone marrow, and extracellular matrix.

Some embodiments use cells that are abnormal in some way. Examples include cells that have been genetically engineered, transformed cells, and immortalized cells. Genetic engineering involves programming the cell to express one or more genes (including, but not limited to genes transfected into the cell), repress the expression of one or more genes, or both. One example of genetically engineered cells useful in the present invention is genetically engineered cells that make and secrete one or more desired molecules. In some embodiments, when genetically engineered cells are implanted in an organism, the molecules produced cause a local effect or systemic effect. Examples of molecules produced include all molecules identified above as "substances." In some embodiments, cells produce antigenic materials, allowing the electroprocessed material to cause an immune response. Examples of genetically engineered cells used in the present invention include cells that: inhibit or stimulate inflammation; facilitate healing; resist immunorejection; provide hormone replacement; replace neurotransmitters; inhibit or destroy cancer cells; promote cell growth; inhibit or stimulate formation of blood vessels; augment tissue; and/or supplement or replace neurons, skin, synovial fluid, tendons, cartilage, ligaments, bone, muscle, organs, dura, blood vessels, bone marrow, and extracellular matrix.

"Stem cell" as used herein generally refers to a special type of cell that has a unique capacity to renew itself and to give rise to specialized cell types. Although most cells of the body, such as heart cells or skin cells, are committed to conduct a specific function, a stem cell is uncommitted and remains uncommitted until it receives a signal to develop into a specialized cell. Stem cells can make identical copies of themselves and they can also give rise to mature cell types that have characteristics morphologies and specialized functions. Typically stem cells generate an intermediate cell type or types before they achieve their fully differentiated state. The intermediate cell is called a precursor or progenitor cell. Stem cells can renew themselves mitotically, and can also (by mitosis) give rise to progenitor cells that are capable of differentiation into cellular components of quasi-functional tissues found in adult individuals. Stem cells as used herein include adult stem cells which are undifferentiated cells distributed throughout the body of an adult individual in a variety of differentiated tissues, including peripheral blood, blood and bone marrow derived hematopoietic, stromal and mesenchymal stem cells. Hematopoietic stem cells existing in adult bone marrow for example can populate the cerebral cortex with highly differentiated Purkinje cell neurons, which are central to the function of normal cortical neural circuits (Wagers et al., Science, 297: 2256 (2002)).

As used herein, a "progenitor cell" intends a cell capable of participating in the process of the regeneration of healthy tissue. "Progenitor cells" are among the daughter cells from mitosis of stem cells. These cells are distinguished from stem cells by commitment to a differentiation program (stimulated by a variety of agents) that produces partially differentiated families of cell classes. These cell classes ultimately regenerate a specific tissue with cells of a fully differentiated and specialized phenotype normally found in the parenchyma of that tissue. For example, cardiac myocytes, skeletal myoblasts, alpha, beta, and delta cells of the pancreas, hepatocytes, neurons, astroglia, oligodendroglia, and microglia of the central nervous system may all descend from bone marrow stem cells and adult stem cells of local tissue origin and remain in the differentiated tissue of the particular organ. This list is merely exemplary and non-limiting, but each of these cells has the capability of initiating tissue regeneration. Further examples of progenitor cells are partially differentiated cells within the adult brain that are daughters of neural adult stem cells that reside in specific regions (e.g., the dentate gyrus of the hippocampus and the subventricular zone). These partially differentiated cells migrate to distant regions of the brain. These cells are committed to become either fully differentiated neurons, or specific types of glial cells, at these distant sites. The neurons take on normal functions within the neural circuitry. The glial cells perform differentiated functions characteristic of glial type. For example, oligodendroglial cells carry out a program of creating myelin, an essential extracellular matrix component in the CNS which electrically insulates the axons of neurons. Satellite cells are progenitors of skeletal muscle fibers and typically reside near the surface of differentiated muscle fibers. Satellite cells enter mitosis and fuse to form differentiated, multinucleated muscle fibers. Progenitor cells can be attracted to a particular tissue region of interest by the presence of an appropriate chemoattractant to begin the process of regeneration of healthy tissue.

"Accessory cell" as used herein refers to a cell that is involved in the regeneration of parenchymal cells, but that is not a parenchymal cell, stem cell, or parenchymal cell progenitor; the accessory cell synthesizes and secretes biological factors that stimulate stem cells and progenitor cells (for example, bone marrow stromal cells, functioning as accessory cells, produce hepatocyte growth factor (HGF), which prevents neuron apoptosis, and nerve growth factor (NGF), neurotropin 4 (NT4), and brain-derived neurotrophic factor (BDNF), all of which stimulate proliferation and differentiation of neuronal progenitors, and suppress apoptosis of differentiated neurons; the accessory cell synthesizes and secretes extracellular matrix components essential to the functional architecture of the parenchymal tissue; the accessory cell synthesizes and secretes biological agents which modify and remodel the extracellular matrix to facilitate parenchymal regeneration from damaged tissue; examples of accessory cells include but are not limited to the following: (a) tissue macrophages derived from circulating blood monocytes; (b) bone marrow stromal cells which give rise to mesenchymal cells in regenerating tissues; (c) microglia resident in the central nervous system.

Genetic engineering can involve, for example, adding or removing genetic material to or from a cell, altering existing genetic material, or both. Embodiments in which cells are transfected or otherwise engineered to express a gene can use transiently or permanently transfected genes, or both. Gene sequences may be full or partial length, cloned or naturally occurring.

The term "interaction" includes the direct interaction between the cells and the scaffold such as, for example, attachment and also the indirect interaction wherein cells interact with the scaffold by using soluble material of the scaffolds (e.g., growth factors) without contacting the surface of the scaffold.

In preferred embodiments, cells in the biologically active scaffold differentiate in histiotypic fashion, i.e., the cells exhibit characteristics and functions typical of such cells in vivo. Examples include, but are not limited to: neurons in basement membrane type matrix, osteoblasts that differentiate and produce hydroxyapatite; and muscle cells that arrange into muscle fibers, chondrocytes that cause formation in the matrix of lacunae of the type characteristic of cartilage in vivo. Embodiments in which cells exhibit either normal, abnormal, or a combination of normal and abnormal characteristics are included within the present invention.

Crosslinking is one of many factors that permit control of the mechanical properties of the scaffold obtained using the methods on the invention. Agent suitable for crosslinking and methods of crosslinking are known in the art (see, for example U.S. Patent Application Publication No. 2004/0037813A1 to Simpson et al. incorporated herein in its entirety). In preferred embodiments, mechanical properties of the scaffolds of the invention are within ranges found within natural extracellular matrix materials and tissues. Examples include, but are not limited to, matrices with an elastic modulus between about 0.5 and about 10 MPa when hydrated and matrices with an elastic modulus between about 2 and about 10 MPa when hydrated.

The ability to combine the unfractionated extracellular matrix extract of the invention or the biologically active scaffold of the invention with additional substances provides numerous advantages. In some embodiments, the non-limiting examples of additional substances include fibrin, elastin, laminin, fibronectin, integrin, hyaluronic acid, chondroitin 4-sulfate, chondroitin 6-sulfate, dermatan sulfate, heparin sulfate, heparin, and keratan sulfate, and proteoglycans in appropriate relative amounts to mimic the composition of extracellular matrix materials. In some embodiments, the matrix contains a variety of structural and regulatory elements that may be needed to promote activities such as healing, regeneration, and cell differentiation.

Other additional substances can be included in the scaffold to provide various properties. One example is the ability to control the persistence or biodegradation of the implanted scaffold. Fibrin as a matrix material tends to degrade faster when implanted than collagen, while some synthetic polymers tend to degrade more slowly. Controlling the relative content of these materials will affect the rate at which the matrix degrades. As another example, materials may be included to increase the susceptibility of a matrix or construct formed from a matrix to heat sealing, chemical sealing, and application of mechanical pressure or a combination thereof. It has been observed that inclusion of synthetic polymers enhances the ability of matrices to be cauterized or heat sealed. The inclusion of electrically or magnetically reactive polymers in matrix materials is another example. In some embodiments, such polymers are used to prepare scaffolds that are conductive, that provide a piezoelectric effect, or that alter the shape, porosity and/or density of the unfractionated extracellular matrix extract processed as described in the invention in response to an electric or magnetic field. Another example is the use of matrix material known to have therapeutic effects. For example, fibrin matrix material assists in arrest of bleeding. Fibrin is a component of the provisional matrix that is laid down during the early stages of healing and may also promote the growth of vasculature in adjacent regions, and in many other ways is a natural healing promoter.

The ability to incorporate additional substances into the scaffold of the invention allows for additional benefits. One such benefit is even closer mimicry of tissue and greater compatibility for implants. In some preferred embodiments, stem cells, committed stem cells that will differentiate into the desired cell type, or differentiated cells of the desired type, are incorporated to more closely mimic tissue.

Additional substances that can provide favorable scaffold characteristics also include drugs and other substances that can produce a therapeutic or other physiological effect on cells and tissues within or surrounding an implant. Any such substance may be used. In many preferred embodiments, substances are included in the scaffold of the invention that will improve its performance when implanted. Examples of substances that can be used include but are not limited to peptide growth factors, antibiotics, and/or anti-rejection drugs. Chemicals that affect cell function, such as oligonucleotides, promoters or inhibitors of cell adhesion, hormones, and growth factor are additional examples of substances that can be incorporated into the scaffold and the release of those substances from the scaffold can provide a means of controlling expression or other functions of cells in the scaffold. Alternatively, cells that are engineered to manufacture desired compounds can be included. The entire construct is, for example, cultured in a bioreactor or conventional culture or placed directly in vivo. For example, neovascularization can be stimulated by angiogenic and growth-promoting factors, administered, as peptides, proteins or as gene therapy. Angiogenic agents can be incorporated into the scaffold. Alternatively, where neovascularization is not desired, antiangiogenic materials, such as angiostatin, may be included in the scaffold. Nerve growth factors can be added to into the unfractionated extracellular matrix extract to promote growth or neurons into the scaffold and tissue. In a degradable scaffold, the gradual degradation/breakdown of the matrix will release these factors and accelerate growth of desired tissues.

Even though, the unfractionated extracellular matrix extract is capable of supporting cell differentiation without additional substances, in certain embodiments, additional substances can be incorporated into the scaffold to regulate differentiation of cells in the matrix. Oligonucleotides and peptides drugs such as retinoic acid are examples of such substances. Oligonucleotide DNA or messenger RNA sequences coding for specific proteins in the sense and antisense direction can also be used. For example, where expression of a protein is desired, sense oligonucleotides can be provided for uptake by cells and expression. Antisense oligonucleotides can be released, for example, to suppress the expression gene sequences of interest. Implants can be designed such that the substances affect cells contained within the matrix, outside the matrix or both.

Several methods exist for studying and quantifying specific characteristics of the unfractionated extracellular matrix extract of the present invention. The fiber diameter and pore dimensions (porosity) for the unfractionated ECM based scaffolds of the invention can be determined, for example, by SEM micrograph that are digitized and analyzed with UTHSCSA ImageTool 2.0 (NIH Shareware). Water permeability, a characteristic that differs from porosity, may also be studied using standard methods. Atomic force microscopy can also be used to prepare three-dimensional images of surface topography of biological specimens in ambient liquid or gas environments and over a large range of temperatures. This tool allows determination of relationship and interaction between matrix components. Construct composition analysis can include, for example, histology analysis to determine the degree of cellular distribution through the constructs interstitial space. To assist this analysis, cells may be stained with any known cell staining technique (for example, hematoxylin and eosin and Masson's trichrome). Cell proliferative activity of cells can be studied, for example, by labeling cells biosynthetically with a label that is incorporated into calls actively undergoing DNA synthesis (for example, with bromodeoxyurdine) and using anti-label antibodies to determine the extent to which cells are undergoing nuclear division. Cellular density may be determined, for example, by measuring the amount of DNA in enzyme-digested samples utilizing known techniques. Degree of degradation or remodeling of the scaffold matrix by cells may be determined by, for example, measuring expression and activity of matrix metalloproteinases from cells. One way of measuring functionality of cells in the processed unfractionated extracellular matrix extract is by measuring various physiological endpoints characteristic of the tissues. For example, muscle cells may be stimulated with an electrical signal or challenged with chemical agents or drugs, for example carbachol, to determine the contractability of a construct. Function of cells in an endocrine construct can be determined by measuring production of the desired hormones. One skilled in the art will understand that the foregoing list is not exhaustive and numerous parameters and endpoints can be used in characterizing tissues and matrices using existing methods.

In embodiments in which the substances for admixing with the unfractionated extracellular matrix extract or deposited onto the scaffold are molecules, any molecule can be used. Molecules may, for example, be organic or inorganic and may be in a solid, semisolid, liquid, or gas phase. Molecules may be present in combinations or mixtures with other molecules, and may be in solution, suspension, or any other form. Examples of classes of molecules that may be used include human or veterinary therapeutics, cosmetics, nutraceuticals, agriculturals such as herbicides, pesticides and fertilizers, vitamins, salts, electrolytes, amino acids, peptides, polypeptides, proteins, carbohydrates, lipids, nucleic acids, glycoproteins, lipoproteins, glycolipids, glycosaminoglycans, proteoglycans, growth factors, hormones, neurotransmitters, pheromones, chalones, prostaglandins, immunoglobulins, monokines and other cytokines, humectants, metals, gases, minerals, plasticizers, ions, electrically and magnetically reactive materials, light sensitive materials, anti-oxidants, molecules that may be metabolized as a source of cellular energy, antigens, and any molecules that can cause a cellular or physiological response. Any combination of molecules can be used, as well as agonists or antagonists of these molecules.

Several preferred embodiments include use of any therapeutic molecule including, without limitation, any pharmaceutical or drug. Examples of pharmaceuticals include, but are not limited to, anesthetics, hypnotics, sedatives and sleep inducers, antipsychotics, antidepressants, antiallergics, antianginals, antiarthritics, antiasthmatics, antidiabetics, antidiarrheal drugs, anticonvulsants, antigout drugs, antihistamines, antipruritics, emetics, antiemetics, antispasmodics, appetite suppressants, neuroactive substances, neurotransmitter agonists, antagonists, receptor blockers and reuptake modulators, beta-adrenergic blockers, calcium channel blockers, disulfiram and disulfiram-like drugs, muscle relaxants, analgesics, antipyretics, stimulants, anticholinesterase agents, parasympathomimetic agents, hormones, anticoagulants, antithrombotics, thrombolytics, immunoglobulins, immunosuppressants, hormone agonists/antagonists, vitamins, antimicrobial agents, antineoplastics, antacids, digestants, laxatives, cathartics, antiseptics, diuretics, disinfectants, fungicides, ectoparasiticides, antiparasitics, heavy metals, heavy metal antagonists, chelating agents, gases and vapors, alkaloids, salts, ions, autacoids, digitalis, cardiac glycosides, antiarrhythmics, antihypertensives, vasodilators, vasoconstrictors, antimuscarinics, ganglionic stimulating agents, ganglionic blocking agents, neuromuscular blocking agents, adrenergic nerve inhibitors, anti-oxidants, vitamins, cosmetics, anti-inflammatories, wound care products, antithrombogenic agents, antitumoral agents, antiangiogenic agents, anesthetics, antigenic agents, wound healing agents, plant extracts, growth factors, emollients, humectants, rejection/anti-rejection drugs, spermicides, conditioners, antibacterial agents, antifungal agents, antiviral agents, antibiotics, tranquilizers, cholesterol-reducing drugs, antitussives, histamine-blocking drugs, monoamine oxidase inhibitor. All substances listed by the U.S. Pharmacopeia are also included within the substances of the present invention.

Other preferred embodiments involve the use of growth factors. Growth factors useful in the present invention include, but are not limited to, transforming growth factor-alpha (TGF-alpha), transforming growth factor-beta (TGF-beta), platelet-derived growth factors including the AA, AB and BB isoforms (PDGF), fibroblast growth factors (FGF), including FGF acidic isoforms 1 and 2, FGF basic form 2, and FGF 4, 8, 9 and 10, nerve growth factors (NGF) including NGF 2.5 s, NGF 7.0 s and beta NGF and neurotrophins, brain derived neutotrophic factor, cartilage derived factor, bone growth factors (BGF), basic fibroblast growth factor, insulin-like growth factor (IGF), vascularendothelial growth factor (VEGF), granulocyte colony stimulating factor (G-CSF), insulin like growth factor (IGF) I and II, hepatocyte growth factor, glial neurotrophic growth factor (GDNF), stem cell factor (SCF), keratinocyte growth factor (KGF), transforming growth factors (TGF), including TGFs alpha, beta, beta1, beta2, and beta3, skeletal growth factor, bone matrix derived growth factors, and bone derived growth factors and mixtures thereof.

Cytokines useful in the present invention include, but are not limited to, cardiotrophin, stromal cell derived factor, macrophage derived chemokine (MDC), melanoma growth stimulatory activity (MGSA), macrophage inflammatory proteins 1 alpha (MIP-1alpha), 2, 3 alpha, 3 beta, 4 and 5, IL-1, IL-2, IL-3, IL-4, IL-5, IL-6, IL-7, IL-8, IL-9, IL-10, IL-11, IL-12, IL-13, TNF-.alpha., and TNF-.beta. Immunoglobulins useful in the present invention include, but are not limited to, IgG, IgA, IgM, IgD, IgE, and mixtures thereof. Some preferred growth factors include VEGF (vascular endothelial growth factor), NGFs (nerve growth factors), PDGF-AA, PDGF-BB, PDGF-AB, FGFb, FGFa, and BGF.

Other molecules useful as substances in the present invention include, but are not limited to, growth hormones, leptin, leukemia inhibitory factor (LIF), tumor necrosis factor alpha and beta, endostatin, angiostatin, thrombospondin, osteogenic protein-1, bone morphogenetic proteins 2 and 7, osteonectin, somatomedin-like peptide, osteocalcin, interferon alpha, interferon alpha A, interferon beta, interferon gamma, interferon 1 alpha, and interleukins 2, 3, 4, 5 6, 7, 8, 9, 10, 11, 12, 13, 15, 16, 17 and 18.

Embodiments involving amino acids, peptides, polypeptides, and proteins may include any type of such molecules of any size and complexity as well as combinations of such molecules. Examples include, but are not limited to, structural proteins, enzymes, and peptide hormones. These compounds can serve a variety of functions. In some embodiments, the matrix may contain peptides containing a sequence that suppresses enzyme activity through competition for the active site. In other applications antigenic agents that promote an immune response and invoke immunity can be incorporated into a construct.

For substances such as nucleic acids, any nucleic acid can be present. Examples include, but are not limited to deoxyribonucleic acid (DNA), ent-DNA, and ribonucleic acid (RNA). Embodiments involving DNA include, but are not limited to, cDNA sequences, natural DNA sequences from any source, and sense or anti-sense oligonucleotides. For example, DNA can be naked (e.g., U.S. Pat. Nos. 5,580,859; 5,910,488) or complexed or encapsulated (e.g., U.S. Pat. Nos. 5,908,777; 5,787,567). DNA can be present in vectors of any kind, for example in a viral or plasmid vector. In some embodiments, nucleic acids used will serve to promote or to inhibit the expression of genes in cells inside and/or outside the processed matrix. The nucleic acids can be in any form that is effective to enhance uptake into cells.

Additional substances further include imaging agents, fluorescence dyes, and the like.

Additional substances in the unfractionated extracellular matrix extract compositions of the present invention or the processed matrix also comprise objects. Examples of objects include, but are not limited to, cell fragments, cell debris, organelles and other cell components, tablets, and viruses as well as vesicles, liposomes, capsules, nanoparticles, and other structures that serve as an enclosure for molecules. In some embodiments, the objects constitute vesicles, liposomes, capsules, or other enclosures that contain compounds that are released at a time after electroprocessing, such as at the time of implantation or upon later stimulation or interaction. In one illustrative embodiment, transfection agents such as liposomes contain desired nucleotide sequences to be incorporated into cells that are located in or the unfractionated extracellular matrix extract compositions of the present invention or the processed matrix. In other embodiments, cell fragments, specific cell fractions or cell debris are incorporated into the matrix or the extract. The presence of cell fragments is known to promote healing in some tissues.

Magnetically or electrically reactive materials are also examples of substances that are optionally included within the unfractionated extracellular matrix extract compositions of the present invention or the scaffolds of the present invention. Examples of magnetically active materials include but are not limited to ferrofluids (colloidal suspensions of magnetic particles), and various dispersions of electrically conducting polymers. Ferrofluids containing particles approximately 10 nm in diameter, polymer-encapsulated magnetic particles about 1-2 microns in diameter, and polymers with a glass transition temperature below room temperature are particularly useful. Examples of electrically active materials are polymers including, but not limited to, electrically conducting polymers such as polyanilines and polypyrroles, ionically conducting polymers such as sulfonated polyacrylamides are related materials, and electrical conductors such as carbon black, graphite, carbon nanotubes, metal particles, and metal-coated plastic or ceramic materials.

In other embodiments, some substances in the unfractionated extracellular matrix extract compositions of the present invention or the processed compositions of the present invention supplement or augment the function of other substances. For example, when the composition comprises cells that express a specific gene, the composition can contain oligonucleotides that are taken up by the cells and affect gene expression in the cells. Fibronectin is optionally incorporated into the matrix to increase cellular uptake of oligonucleotides by pinocytosis.

The scaffold itself can provide a therapeutic effect. The invention thus includes embodiments involving methods of causing a therapeutic effect through delivery of a processed material to a location without incorporating additional substances in the processed material.

Cells

The order of admixing cells with the unfractionated extracellular matrix extract of the scaffold may vary depending on the desired application and the known condition of cell growth. For example, hair follicle, sertoli cells and the like are apt to be better cultured if first dispersed in the liquid phase prior to polymerization whereas epithelial cells, exocrine acinar cells, sciatic nerve cell, spinal cord neuron, thyroid organ culture, and the like are better cultured on top of the formed scaffold. Cells can be added to the unfractionated extracellular matrix extract prior to the processing method (i.e., electrospinning, lyophilizing, CPD or combination thereof), during the processing or after the processing. A person skilled in the art would appreciate that survival of processing conditions may produce inconsistent results if cells are added prior to the processing steps in making the scaffold wherein some cells are more resilient than others when exposed to change in chemical (e.g., solvents) and physical (e.g., temperature and pressure) parameters. In certain embodiments, promoting the growth of some cell types is achieved inoculating or dispersing the cells in the cold liquid extract just before gel formation (e.g., in case of a hydrogel in electroprocessing). In certain embodiments, cells are added to the unfractionated extracellular matrix extract prior to the freezing step. In a preferred embodiment, the cells are added to the scaffold after it is made.

Methods of Making Biologically Active Scaffold—Electroprocessed Scaffolds

The methods of making the electroprocessed scaffolds of the invention include electroprocessing the unfractionated extracellular matrix extract of the invention and optionally electroprocessing it with other additional substances. As defined above, one or more electroprocessing techniques, such as electrospin, electrospray, electroaerosol, electrosputter, or any combination thereof, may be employed to make the electroprocessed scaffold of the present invention. Electroprocessing apparatuses are known in the art and described, for example in U.S. Patent Application Publication No. 2004/0037813A1 to Simpson et al. Basically, the electroprocessing apparatus for electroprocessing material includes an electrodepositing mechanism and a target substrate. The electrodepositing mechanism includes a reservoir or reservoirs to hold the one or more solutions that are to be electroprocessed or electrodeposited. The reservoir or reservoirs have at least one orifice or nozzle to allow the streaming of the solution from the reservoirs. Although the terms "orifice" and "nozzle" are used throughout, these term are not intended to be limiting, and refer generically to any location from which solutions may stream during electroprocessing. One or a plurality of nozzles may be configured in an electroprocessing apparatus. If there are multiple nozzles, each nozzle is attached to one or more reservoirs containing the same or different solutions. Similarly, there can be a single nozzle that is connected to multiple reservoirs containing the same or different solutions. Multiple nozzles may be connected to a single reservoir. Because different embodiments involve single or multiple nozzles and/or reservoirs, any references herein to one or nozzles or reservoirs should be considered as referring to embodiments involving single nozzles, reservoirs, and related equipment as well as embodiments involving plural nozzles, reservoirs, and related equipment. The size of the nozzles can be varied to provide for increased or decreased flow of solutions out of the nozzles. One or more pumps used in connection with the reservoirs can be used to control the flow of solution streaming from the reservoir through the nozzle or nozzles. The pump can be programmed to increase or decrease the flow at different points during electroprocessing. In this invention pumps are not necessary but provide a useful method to control the rate at which material is delivered to the electric field for processing. Material can be actively delivered to the electric field as a preformed aerosol using devices such as air brushes, thereby increasing the rate of electrodeposition and providing novel combinations of materials. Nozzles may be programmed to deliver material simultaneously or in sequence.

The electroprocessing occurs due to the presence of a charge in either the orifices or the target, while the other is grounded. In some embodiments, the nozzle or orifice is charged and the target is shown to be grounded. Those of skill in the electroprocessing arts will recognize that the nozzle and solution can be grounded and the target can be electrically charged. The creation of the electrical field and the effect of the electrical field on the electroprocessed materials or substances that will form the electroprocessed composition occur whether the charge is found in the solution or in the grounded target. In different embodiments, the space between the target and the nozzle or source of the materials can contain air or selected gases. In various embodiments, the space can be maintained under a vacuum or below atmospheric pressure or above normal atmospheric pressure. Solvents used in electroprocessing typically evaporate during the process. This is considered advantageous because it assures that the electroprocessed materials are dry. In embodiments using water or other less volatile solvents, electroprocessing may optionally occur in a vacuum or other controlled atmosphere (for example, an atmosphere containing ammonia) to assist evaporation. Electroprocessing can be oriented varying ways with respect to gravity forces or occur in a zero gravity environment.

The substrate can also be used as a variable feature in the electroprocessing of materials used to make the electroprocessed composition. Specifically, the target can be the actual substrate for the materials used to make electroprocessed matrix, or electroprocessed matrix itself is deposited. Alternatively, a substrate can be disposed between the target and the nozzles. For instance, a petri dish can be disposed between nozzles and a target, and a matrix can be formed in the dish. Other variations include but are not limited to non-stick surfaces between the nozzles and target and placing tissues or surgical fields between the target and nozzles. The target can also be specifically charged or grounded along a preselected pattern so that the solution streamed from the orifice is directed into specific directions. The electric field can be controlled by a microprocessor to create an electroprocessed matrix having a desired geometry. The target and the nozzle or nozzles can be engineered to be movable with respect to each other, thereby allowing additional control over the geometry of the electroprocessed matrix to be formed. The entire process can be controlled by a microprocessor that is programmed with specific parameters that produce a specific preselected electroprocessed matrix. It is to be understood that any electroprocessing technique may be used, alone or in combination with another electroprocessing technique, to make the compositions of the present invention.

Electroprocessed biologically active scaffolds of the invention are produced from the lyophilized unfractionated extracellular matrix extract in a liquid suspension or solution, gelatin, particulate suspension, or hydrated gel. Where fibrin is also electroprocessed, the fibrin may be used as a preformed gel electroprocessed by subjecting it to pressure, for example by using a syringe or airbrush apparatus with a pressure head behind it to extrude the fibrin gel into the electrical field. In general, when producing fibers using electroprocessing techniques, especially electrospinning, it is preferable to use the monomer of the polymer fiber to be formed. In some embodiments it is desirable to use monomers to produce finer filaments. In other embodiments, it is desirable to include partial fibers to add material strength to the matrix and to provide additional sites for incorporating substances. Matrix materials such as collagen in a gelatin form may be used to improve the ability of the material to dissolve. Acid extraction method can be used in preparing such gels to maintain the structure of the monomeric subunits. Units can then be treated with enzymes to alter the structure of the monomers.

The present invention relates to an electroprocessing method of making a biologically active three-dimensional scaffold capable of supporting growth and differentiation of a cell, the method comprising: providing an unfractionated extracellular matrix extract from a mammalian tissue; freezing the unfractionated aqueous extracellular matrix extract at a temperature of at most −60° C. and freeze drying under a negative pressure to provide a lyophilized unfractionated extracellular matrix extract; combining the lyophilized unfractionated extracellular matrix extract with an aqueous or non-aqueous solvent to form a solution, a hydrogel or a suspension; electroprocessing the lyophilized unfractionated extracellular matrix extract in a form of a solution, a hydrogel or a suspension and thereby making the biologically active three-dimensional scaffold comprising at least one of fibers or droplets.

In certain embodiments of the electroprocessing method, the unfractionated extracellular matrix extract is provided in an aqueous medium.

In certain embodiments of the electroprocessing method, said freezing the unfractionated aqueous extracellular matrix extract is conducted at a temperature of from −80° C. to −130° C.

In certain embodiments of the electroprocessing method, the method further comprises electroprocessing the lyophilized unfractionated extracellular matrix extract into a mold.

In certain embodiments of the electroprocessing method, the method further comprises crosslinking the lyophilized unfractionated extracellular matrix extract subsequent to said electroprocessing, wherein the lyophilized unfractionated extracellular matrix extract is contacted with a crosslinker.

In certain embodiments of the electroprocessing method, the unfractionated extracellular matrix extract is derived from a basement membrane.

In certain embodiments of the electroprocessing method, the unfractionated extracellular matrix extract comprises about 60-85% laminin, 5-30% collagen IV, 1-10% nidogen, 1-10% heparan sulfate proteoglycan and 1-5% entactin by weight.

In certain embodiments of the electroprocessing method, the unfractionated extracellular matrix extract comprises less than 50% collagen I, collagen II or collagen III cumulatively or singly.

In certain embodiments of the electroprocessing method, the biologically active three dimensional scaffold consists essentially of 60-85% laminin, 5-30% collagen IV, 1-10% nidogen, 1-10% heparan sulfate proteoglycan and 1-5% entactin by weight.

In certain embodiments of the electroprocessing method, the unfractionated extracellular matrix extract further comprises an additional substance. In certain embodiments, the additional substance is at least one of a cell, a pharmaceutical agent, an imaging agent, a biologically active agent and a polymer.

In certain embodiments of the electroprocessing method, the basement membrane is derived from at least one of an Engelberth-Holm-Swarm tumor, human placenta, mammalian Decemet's membrane, mammalian kidney epithelium, and mammalian small intestinal submucosa.

In another aspect, the invention relates to a biologically active three-dimensional scaffold made by the electroprocessing method. In certain embodiments, the biologically active three-dimensional scaffold includes fibers or droplets which have an average diameter of between about 30 nm and about 1 μm. In certain embodiments, the unfractionated extracellular matrix extract comprises about 60-85% laminin, 5-30% collagen IV, 1-10% nidogen, 1-10% heparan sulfate proteoglycan and 1-5% entactin by weight. In certain embodiments, the unfractionated extracellular matrix extract comprises less than 50% collagen I, collagen II or collagen III cumulatively or singly. In certain embodiments, the unfractionated extracellular matrix extract consists essentially of 60-85% laminin, 5-30% collagen IV, 1-10% nidogen, 1-10% heparan sulfate proteoglycan and 1-5% entactin by weight.

In another aspect, the invention relates to an engineered tissue made by contacting the biologically active three-dimensional scaffold made by the electroprocessing method with cells in vivo or in vitro under conditions effective to allow interaction between the biologically active three-dimensional scaffold and the cells. In certain embodiments, the cells are members selected from the group consisting of stem cells, progenitor cells, and differentiated cells. In certain embodiments, the cells are at least one of neural cells, epithelial cells, cardiac myocytes, pulmonary lung cells, keratinocytes, endothelial cells. In certain embodiments, the cells are PC12 or neuronal-restricted precursor (NRP) cells and the engineered tissue is a neurone producing tissue.

In certain embodiments, the unfractionated extracellular matrix extract comprises about 60-85% laminin, 5-30% collagen IV, 1-10% nidogen, 1-10% heparan sulfate proteoglycan and 1-5% entactin by weight. In certain embodiments, the unfractionated extracellular matrix extract comprises less than 50% collagen I, collagen II or collagen III cumulatively or singly. In certain embodiments, the unfractionated extracellular matrix extract consists essentially of 60-85% laminin, 5-30% collagen IV, 1-10% nidogen, 1-10% heparan sulfate proteoglycan and 1-5% entactin by weight. In certain embodiments, the engineered tissue further comprising an additional substance. Non-limiting examples of such substances include a cell, a pharmaceutical agent, an imaging agent, a biologically active agent and a polymer.

In embodiments in which two materials combine to form a third material, the solutions containing these components can be mixed together immediately before they are streamed from an orifice in the electroprocessing procedure. In this way, the third material forms literally as the microfibers or microdroplets are formed in the electrospinning process. Alternatively, such matrices can be formed by electrospraying a molecule that can form matrix materials into a moist or otherwise controlled atmosphere of other molecules necessary to allow formation of the matrix to form filaments within the electric field.

Alternatively, in embodiments in which two or more matrix materials are combined to form a third, the matrix materials can be electroprocessed in conjunction with or separately from each other. In some desirable embodiments, this occurs under conditions that do not allow the two molecules to form the third molecule until the desired time. This can be accomplished several ways. Alternatively, molecules can be mixed with a carrier, such as PEO, or other synthetic or natural polymers such as collagen. The carrier acts to hold the reactants in place until they are initiated.

Lyophilization or Freeze Drying Method

In another aspect of the invention, the scaffolds are prepared by a freeze-drying method wherein the frozen material is dried under vacuum preserving chemical and biological properties of the ECM extract capable of supporting growth and differentiation of a cell.

In this method, the unfractionated extracellular matrix extract is frozen and lyophilized (i.e., freeze dried). In particular, the unfractionated extracellular matrix extract is frozen at a controlled rate of temperature drop to control the size of the formed ice crystals. Once frozen, and without allowing the material to thaw, the lyophilization process sublimes the ice crystals directly to a vapor under vacuum and low temperatures. This leaves voids or interstices in the spaces previously occupied by the ice crystals. The terms "freeze dry" and "lyophilization" when referred to the process described herein are used interchangeably.

In the lyophilization method of making a biologically active three-dimensional scaffold, the method includes: providing an unfractionated extracellular matrix extract from a mammalian tissue in a form of a powder, a solution, a hydrogel or a suspension; placing the unfractionated extracellular matrix extract in a mold; freezing the unfractionated extra cellular matrix extract at 0° C. or below at a controlled freezing rate; freeze-drying the unfractionated extra cellular matrix extract by subjecting the unfractionated extracellular matrix extract to a temperature of at most −60° C. for a time sufficient to remove at least 90% of a liquid from the unfractionated extracellular matrix extract and thereby obtaining a lyophilized unfractionated extracellular matrix extract; and optionally crosslinking the lyophilized unfractionated extracellular matrix extract by contacting with a crosslinker and thereby providing the biologically active three-dimensional scaffold having porous morphology.

In certain embodiments of the method, freeze-drying is conducted at a temperature of between about −130° C. to about −80° C. In certain embodiments of the method, the unfractionated extracellular matrix extract is provided in an organic solvent. In certain embodiments of the method, the unfractionated extracellular matrix extract is provided in an aqueous medium. In certain embodiments, the method further comprises crosslinking the lyophilized unfractionated extracellular matrix extract by contacting with a crosslinker.

In yet another aspect, the invention relates to a biologically active three-dimensional scaffold made by the lyophilization method. In certain embodiments, the pores have an average diameter of between about 10 μm and about 200 μm. In certain embodiments, the average diameter of pores is between about 50 μm and about 120 μm.

In certain embodiments, at least 45% of the biologically active three dimensional scaffold comprise pores. In certain embodiments, at most 95% of the biologically active three dimensional scaffold comprise pores. In certain embodiments, pores constitute 75% to 85%. In certain embodiments, the matrix comprises pores having an average area of between about 10 square μm and 200 square μm.

In yet another aspect, the invention relates to an engineered tissue made by contacting the biologically active three dimensional scaffold made by the lyophilization method with cells in vivo or in vitro under conditions effective to allow interaction between the biologically active three dimensional scaffold and the cells. In certain embodiments, the cells are members selected from the group consisting of stem cells, progenitor cells, and differentiated cells. In certain embodiments, the cells are at least one of neural cells, epithelial cells, cardiac myocytes, pulmonary lung cells, keratinocytes, endothelial cells. In certain embodiments, the cells are PC12 or neuronal-restricted precursor (NRP) cells and the engineered tissue is a neurone producing tissue.

In certain embodiments, the unfractionated extracellular matrix extract comprises about 60-85% laminin, 5-30% collagen IV, 1-10% nidogen, 1-10% heparan sulfate proteoglycan and 1-5% entactin by weight. In certain embodiments, the unfractionated extracellular matrix extract comprises less than 50% collagen I, collagen II or collagen III cumulatively or singly.

In certain embodiments, the unfractionated extracellular matrix extract consists essentially of 60-85% laminin, 5-30% collagen IV, 1-10% nidogen, 1-10% heparan sulfate proteoglycan and 1-5% entactin by weight. In certain embodiments, the tissue further comprises an additional substance. In certain embodiments, the additional substance is at least one of a cell, a pharmaceutical agent, an imaging agent, a biologically active agent and a polymer.

Any commercially available freezer for freezing the suspension to a desired temperature may be used. Likewise, any commercially available lyophilizer may be used for the lyophilization process. One exemplary machine for performing the lyophilization method is a Virtis Genesis™ Series lyophilizer which is commercially available from SP Industries, Inc. of Gardiner, N.Y. Another exemplary apparatus includes EMITECH K750X Freeze Dry Peltier System and K775X Turbo Freeze Drier (Emitech Ltd., Kent, UK) and Labconco Freeze Dry System (Labonco, New Bruinswick N.J.).

The process parameters of the lyophilization method may be varied to produce scaffolds of varying pore sizes and material densities. For example, the rate at which the suspension is frozen, the amount of water present in the suspension, or the compactness of the extracellular matrix material may be varied to produce scaffolds of varying pore sizes and material densities.

For instance, to produce scaffolds having a relatively large pore size and a relatively low material density, the extracellular matrix suspension may be frozen at a slow, controlled rate (e.g., $-1°$ C./min or less) to a temperature of about $-20°$ C., followed by freezing to $-80°$ C. and lyophilization of the resultant mass. To produce scaffolds having a relatively small pore size and a relatively high material density, the extracellular matrix material may be tightly compacted by centrifuging the material to remove a portion of the liquid (e.g., water or Dulbecco's modified Eagle's medium (DMEM)) in a substantially uniform manner prior to freezing. Thereafter, the resultant mass of extracellular matrix material is flash-frozen using oil or dry ice or liquid nitrogen or another suitable cryogenic medium followed by lyophilization of the mass. To produce scaffolds having a moderate pore size and a moderate material density, the extracellular matrix material is first tightly compacted by centrifuging the material to remove a portion of the liquid (e.g., water) in a substantially uniform manner prior to freezing. Thereafter, the resultant mass of extracellular matrix material is frozen at a relatively fast rate (e.g., $>-1°$ C./min) to a temperature of about $-80°$ C. followed by lyophilization of the mass.

Temperatures lower than $-20°$ C. require longer sublimation time. For some specimens when gentle drying is required, the sample may be initially subjected to a temperature of from about $-80°$ C. to about $-120°$ C.

In certain embodiments, the pore size of lyophilized scaffolds of the invention is in a range of about 10 μm to about 400 μm. Preferably, the pore size is about 20 μm.

In a preferred embodiment, the unfractionated extracellular matrix is dissolved or suspended in water or DMEM, placed in a mold, frozed and freeze dried and then optionally crosslinked by using carbodiimide or other cross-linkers as described above.

Critical Point Drying (CPD)

In another aspect of the invention, the unfractionated extracellular matrix extract is processed into a nanofibrous scaffold by CPD. CPD is a method used conventionally for specimen preparation for scanning electron microscopy. CPD is a method for carbon dioxide (CO2) or other transitional media (e.g., hydrogen, oxygen, nitrogen, carbon monoxide) drying of delicate biomaterials without damaging the structure of the scaffolds by surface tension that occurs when changing from the liquid to the gaseous phase without the effects of surface tension.

The inventors have discovered that nanofibrous scaffolds can be obtained by conducting crosslinking and dehydrating the unfractionated extracellular matrix extract prior to CPD. Without being bound by a specific theory, it is believed that this sequence of steps is necessary to obtain the desired nanofibrous structures, which is different from porous structures obtained by methods known in the art (e.g., US2004/0258729A1).

The inventors have discovered that not only does the unfractionated extracellular matrix extract retain its biological activity, the scaffold comprising fibers sized about 30 nm to about 80 nm in diameter and preferably from 50 nm to 60 nm can be obtained.

In accordance with the method of the invention, the unfractionated extracellular matrix extract is first fixed or crosslinked to preserve the ultrastructure of the bioactive macromolecules and the various ECM molecules, and then dehydrated. e.g., through graded ethanol (50-100%), acetone or other suitable dehydrating fluid.

The dehydrated unfractionated ECM extract in a dehydrating fluid (e.g., an alcohol) is placed in a pressurized container at, for example, 50 bars pressure with the transitional media, preferably liquid carbon dioxide. The alcohol which is the more dense substance shifts to the base of the container and is replaced by the CO2. Thus the solvent within the unfractionated extracellular matrix extract is removed and substituted with liquid carbon dioxide. When the temperature is increased from about 15-20° C. to about 33-40° C. with a consequent increase in pressure (to 90 bars), the liquid carbon dioxide will gasify and escape. This results in a nanofibrous biologically active scaffold comprising fibers sized about 30 nm to about 80 nm in diameter and preferably from 50 nm to 60 nm which retains the internal features dictated by the mold.

The biologically active scaffold can then, if desired, be further crosslinked to increase the mechanical strength, decrease the antigenicity and decrease the degradation rate of the scaffold. Crosslinking can be accomplished by both physical and chemical techniques. Physical crosslinking can be achieved by dehydrothermal treatment and UV or gamma irradiation. Aldehydes such as glutaraldehyde and formaldehyde, polyepoxy resin, acyl azides, carbodiimides and hexamethylene compounds can be used for chemical crosslinking. In yet another aspect, the invention relates to a critical point drying method of making a nanofibrous biologically active three-dimensional scaffold capable of supporting growth and differentiation of a cell, the method comprising: providing an unfractionated extracellular matrix extract of a mammal in a form of a powder, a solution, a hydrogel or a suspension; placing the unfractionated extracellular matrix extract in a mold; crosslinking the unfractionated extracellular matrix extract by contacting with a crosslinker to form a crosslinked unfractionated extracellular matrix extract; contacting the crosslinked unfractionated extracellular matrix extract with a dehydrating substance (e.g., ethanol) to the crosslinked unfractionated extracellular matrix extract to form a dehydrated unfractionated extracellular matrix extract; critical point drying the dehydrated unfractionated extracellular matrix extract with a transitional media to obtain the nanofibrous biologically active three-dimensional scaffold. In certain embodiments, the unfractionated extracellular matrix extract is provided in an aqueous medium. In certain embodiments, said contacting comprises sequentially contacting with graded ethanol. In certain embodiments, the transitional media comprises liquid carbon dioxide.

In certain embodiments, the nanofibrous biologically active three-dimensional scaffold is made of fibers having diameter between 30 and 80 nm.

In certain embodiments, the unfractionated extracellular matrix extract comprises about 60-85% laminin, 5-30% collagen IV, 1-10% nidogen, 1-10% heparan sulfate proteoglycan and 1-5% entactin by weight. In certain embodiments, the unfractionated extracellular matrix extract comprises less than 50% collagen I, collagen II or collagen III cumulatively or singly. In certain embodiments, the unfractionated extracellular matrix extract consists essentially of 60-85% laminin, 5-30% collagen IV, 1-10% nidogen, 1-10% heparan sulfate proteoglycan and 1-5% entactin by weight.

In yet another aspect, the invention relates to an engineered tissue made by contacting the nanofibrous biologically active three-dimensional scaffold made by the critical point drying method with cells in vivo or in vitro under conditions effective to allow interaction between the nanofibrous biologically active three-dimensional scaffold and the cells. In certain embodiments, the cells are members selected from the group consisting of stem cells, progenitor cells, and differentiated cells. In certain embodiments, the cells are at least one of neural cells, epithelial cells, cardiac myocytes, pulmonary lung cells, keratinocytes, endothelial cells. In certain embodiments, the cells are PC12 or neuronal-restricted precursor (NRP) cells and the engineered tissue is a neurone producing tissue. In certain embodiments, the unfractionated extracellular matrix extract comprises about 60-85% laminin, 5-30% collagen IV, 1-10% nidogen, 1-10% heparan sulfate proteoglycan and 1-5% entactin by weight. In certain embodiments, the unfractionated extracellular matrix extract comprises less than 50% collagen I, collagen II or collagen III cumulatively or singly. In certain embodiments, the unfractionated extracellular matrix extract consists essentially of 60-85% laminin, 5-30% collagen IV, 1-10% nidogen, 1-10% heparan sulfate proteoglycan and 1-5% entactin by weight. In certain embodiments, the engineered tissue further comprising an additional substance as described above.

Brain or Spinal Cord Tissue Repair or Regeneration

Damage to brain and spinal cord tissue can result from a variety of situations and conditions, which include infections (such as the various bacterial and viral meningoencephalitides), vascular disorders (such as hemorrhagic and ischemic stroke), degenerative disorders (such as multiple sclerosis, Parkinson's disease Alzheimer's disease) and physical trauma, including concussion of the brain, laceration of the brain, and pressure and crush lesions to the spinal cord.

Accordingly, in one embodiment, the invention contemplates use of the composition for regeneration of brain and spinal cord tissue post-damage or at risk of damage. In yet another aspect, the invention relates to a use of the engineered tissue made by the above described methods for regeneration of brain and spinal cord tissue post-damage or at risk of damage.

In particular, the relevant biologically active scaffold optionally will include a first agent effective to attract essential cells, including but not limited to microglia, oligodendroglia, neural adult stem cells, neurons, bone marrow (BM) cells, accessory cells (AC), smooth muscle cells (SMC), marrow stromal cells (mSC), hematopoietic bone marrow stem cells, (hSC), and astroctyes. Some of these cells can migrate across the blood brain barrier (BBB) and/or are present in the brain tissue. Attraction of accessory cells is known to be essential in the response of the brain to damage. It is known that marrow stromal cells (mSC), marrow hematopoietic stem cells (hSC), other bone marrow (BM) cells, microglia, astroglia, and monocyte-macrophages enter the damaged tissue regions and act as accessory cells (AC), by producing a variety of cytokines and other biological factors which directly induce mitogenesis of stem cells and progenitor cells, and differentiation of progenitors to functioning glia and neurons. Agents effective to attract one or more of these above cells include hepatocyte growth factor (HGF), macrophage chemoattractant protein1-1 (MCP-1), stromal cell-derived factor-1α (SDF-1α), stromal cell-derived factor-1β (SDF-1β), basic fibroblast growth factor (bFGF), epidermal growth factor (EGF), interleukin-1 (IL-1), and platelet-derived growth factor-AB (PDGF-AB).

A second agent can be optionally included in the biologically active scaffold to stimulate a variety of phenomena in the attracted cells, which include: (I) proliferation of stem cells and progenitor cells, (ii) differentiation to functional parenchymal cells, and (iii) production of a variety of cytokines and other biological agents which stimulate proliferation, differentiation, and modulate and coordinate differentiation amongst regenerating glia and neurons. Exemplary stimulatory agents include, but are not limited to neurotrophin 3 (NT3), brain-derived neurotrophic factor (BDNF), nerve growth factor (NGF), epidermal growth factor (EGF), basic fibroblast growth factor (bFGF), NEP1-40 inhibitor of Nogo protein, neurotrophin 4 (NT4), β-mercaptoethanol (β-ME), human leukemia inhibitory factor (hLIF), retinoic acid (RA), interleukin-1 (IL-1), interleukin-6 (IL-6), platelet-derived growth factor-AB (PDGF-AB), transforming growth factor-α (TOF-α), stem cell factor (SCF), vascular endothelial growth factor (VEGF), insulin, forskolin, valproic acid, heparin, hepuran, glycosylated cytostatin-C, and phorbol myristate acetate (TPA).

It is contemplated that the composition may, additionally, include agents which act directly on the tissue extracellular matrix and the blood-brain barrier to allow complete development of regenerated nervous system parenchyma. These agents may act to implement neuronal plasticity, in which parenchymal regeneration is accomplished by re-connection of neuronal networks in configurations different from those in the damaged tissue. Exemplary agents to accomplish these components of regeneration include neurotrophin 3 (NT3), chondroitinase ABC (chABC), NEP1-40 inhibitor of Nogo protein binding, and vascular endothelial growth factor A (VEGF-A).

The biologically active scaffold may also include one or more factors that prolong the survival of the stem cells, progenitor cells, and/or differentiated cells. Factors that prolong survival of cells in brain tissue include, brain-derived neurotrophic factor (BDNF), nerve growth factor (NGF), basic fibroblast growth factor (bFGF), epidermal growth factor (EGF), platelet-derived growth factor-AB (PDGF-AB), glycosylated cytostatin-C, β-mercaptoethanol (β-ME), butylated hydroxyanisole (BHA), dimethyl sulfoxide (DMSO), hepatocyte growth factor (HGF), nerve growth factor, neurotrophin 4 (NT4), butylated hydroxytoluene (BHT), and human leukemia inhibitory factor (hLIF).

The biologically active scaffold may also include ligands to which the surfaces of stem cells, progenitor cells, and other cells can bind. These ligands are contemplated to increase efficiency of regeneration by increasing the number of cells in close proximity to the stimulating factors that are also part of the composition. It is known that binding of stem cells and progenitor cells to cell adhesion moieties of the extracellular matrix promotes mitogenesis and differentiation. Suitable ligands include laminin and vascular cell adhesion molecule 1 (VCAM-1).

In yet another aspect, the invention relates to a method of use the engineered tissue of the invention made by the above described methods for brain or spinal cord tissue repair or regeneration, the method comprises administering the engineered tissue of the invention to a mammal in need of said brain or spinal cord tissue repair or regeneration.

This method will be demonstrated first using a rodent model developed in the University of Pennsylvania, for example.

The invention will be illustrated in more detail with reference to the following Examples, but it should be understood that the present invention is not deemed to be limited thereto.

EXAMPLES

Example 1

Preparation of basement-membrane-derived extracellular composition from EHS mouse tumor can be made using the method described in U.S. Pat. No. 4,829,000.

1. Making buffers:
3.4 M NaCl buffer (stock):

| | |
|---|---|
| 3.4M NaCl | 397 g |
| 2M Tris pH 7.4 | 25 ml |
| 0.004M EDTA | 3.0 g |
| 0.002M NEM | 0.5 g (N-ethylmaleimide) |

Add dd H2O to 2 liters and adjust pH to 7.4
2 M urea buffer (stock):

| | |
|---|---|
| 2M urea | 240 g |
| 0.05M Tris-base | 12.1 g |
| 0.15M NaCl | 18 g |

Add dd H2O to 2 liters and adjust pH to 7.4
Tris-saline buffer (must be fresh):

| | |
|---|---|
| 0.05M Tris-base | 12.1 g |
| 0.15M NaCl | 18.0 g |

Add dd H2O to 2 liters and adjust pH to 7.4
2. Weight 50 g tumor, defrost if require (from −80° C.), and homogenize in 200 ml 3.4M NaCl buffer, all in 4° C. (keep the ratio as 1:2 w/v)
3. Centrifuge at 7000 rpm, 4° C., 15 min, ×3 times. Each time, discard the supernatant and add the same amount of 3.4M NaCl buffer into the centrifuge tube, then balance the weight on ice.
4. Collect the final precipitate, stir in 50 ml 2M urea buffer for overnight at 4° C.
5. The next day, centrifuge at 14,000 rpm, 4° C., for 20 min. SAVE the supernatant.
6. Add to the precipitate urea buffer mix and centrifuge again at 14,000 rpm, 4° C., for 20 min. Combine the supernatant with the previous one.
7. Dialyze the supernatant in 0.05 M Tris-saline buffer with chloroform (for sterilization); 900 ml Tris buffer: 5 ml chloroform; for 2 hrs in 4° C.
8. Change dialyses to Tris-saline buffer alone, rotate the dialyze bag and dialyze for another 2 hrs 4° C.
9. Dialyze last time against media salts such as High-glucose DMEM overnight at 4° C.
10. Aliquot in sterile hood into sterile 15 ml tubes with 5 ml in each tube and freeze in −20° C.
11. For gelation: defrost the tube in 4° C. and when it liquid pour the extract into container and warm for 30 min.
12. To use the gel as a cell culture substratum, add about 3 ml of suitable growth medium on top of the polymerized gel and inoculate the medium with the dispersions of the cells which are desired to be grown. The growth medium to be used will depend on the type of the cell which is desired to be grown; specific standard growth medium and conditions (e.g. $CO_2$ concentration, temperature, pH and the like) for different types of cells being well known in the art.

Example 2

Preparation of basement membrane from human placenta can be made as described in from U.S. Pat. No. 4,829,000.
Extracts comparable in composition and in biological activity can also be obtained from human placenta using a process similar to that used for the EHS mouse tumor described in Example 1. However, since placenta is not composed of pure basement membrane like the EHS mouse tumor, an additional step is necessary as described hereunder:
(a) Placenta is freed of cord and amnion.
(b) Placenta is then washed and homogenized in about 3.4M NaCl in 0.05M Tris-HCl, pH 7.4 containing standard protease inhibitors such as phenylmethyl sulfonyl fluoride; n-ethylmaleimide EDTA, pepstatin and the like.
(c) The tissue residue is extracted overnight at about 4° C. with an equal volume (g/ml) of 0.5M NaCl in 0.05M Tris-HCl, pH 7.4.
(d) The tissue after buffer extraction is washed with an equal volume of the same buffer and combined with the extract.
(e) The tissue residue is extracted overnight at about 4° C. with an equal volume (g/ml) of 2.0M urea in 0.05M Tris-HC, pH 7.4.

Both the 0.5M NaCl extract and the 2.0M urea extract are dialyzed against 0.02M sodium phosphate buffer, pH 7.4 overnight at 4° C. and the dialyzed samples are separately chromatographed on a heparin Sepharose column equilibrated in 0.02M sodium phosphate buffer, pH 7.4, containing 0.15M NaCl. The bound material is eluted with 1.0M NaCl and dialyzed into Eagle's minimal essential medium.

Example 3

Figure 1B:
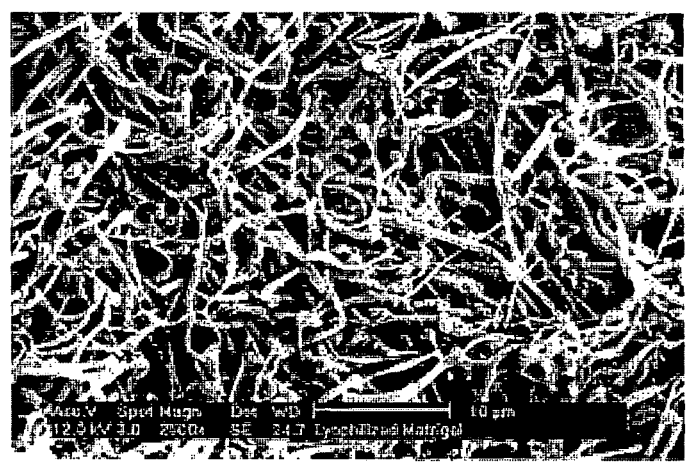
Figure 1C:
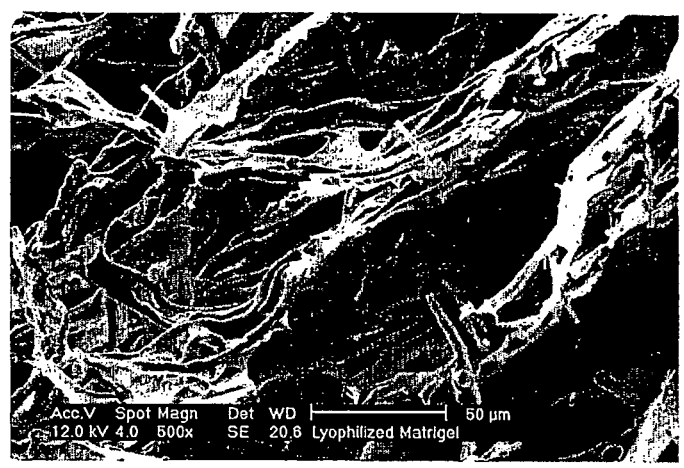
Figure 2:
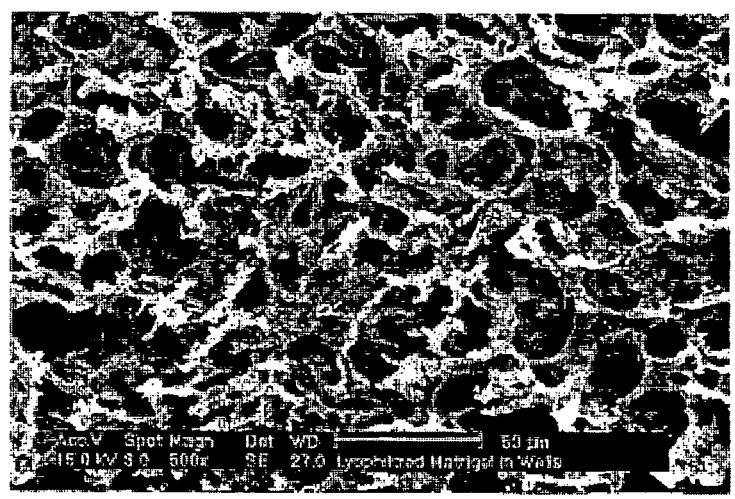
FIG. 2 is a scanning electron micrograph (SEM) of lyophilized MATRIGEL in well (the sample was dialyzed, dissolved and diluted with dd H2O, then lyophilized).
Figure 3A:
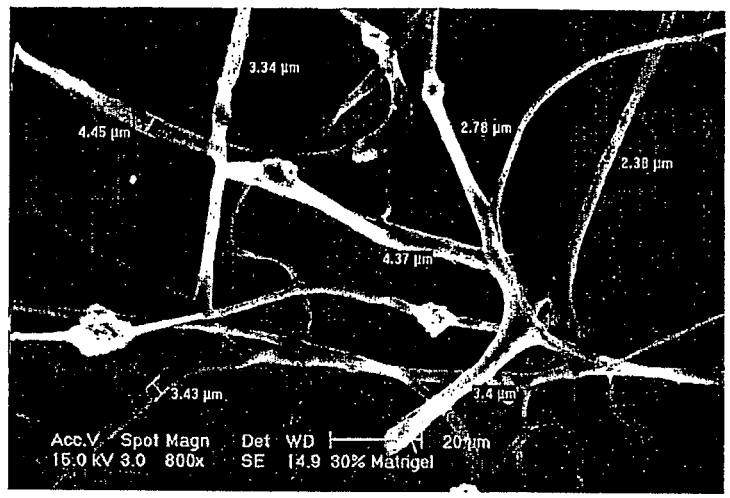
FIG. 3A is an SEM of electrospun MATRIGEL (on microscope slides, SEM-10272004), 30%.
Figure 3B:
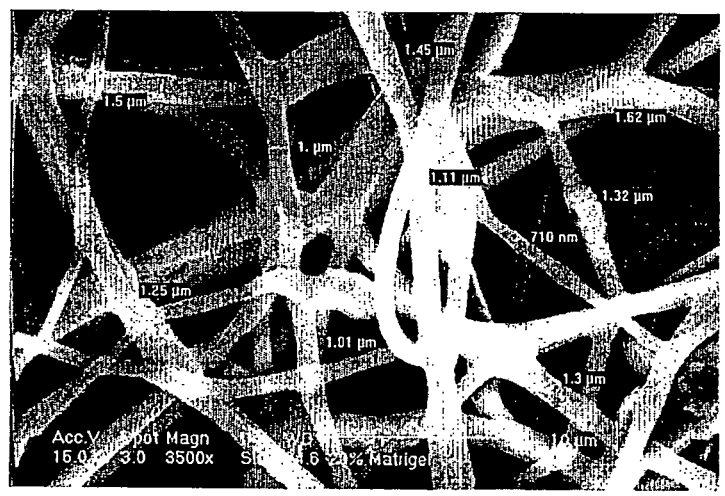
FIG. 3B is an SEM of electrospun MATRIGEL on microscope slides, SEM-10272004), 20%.
Figure 4A:
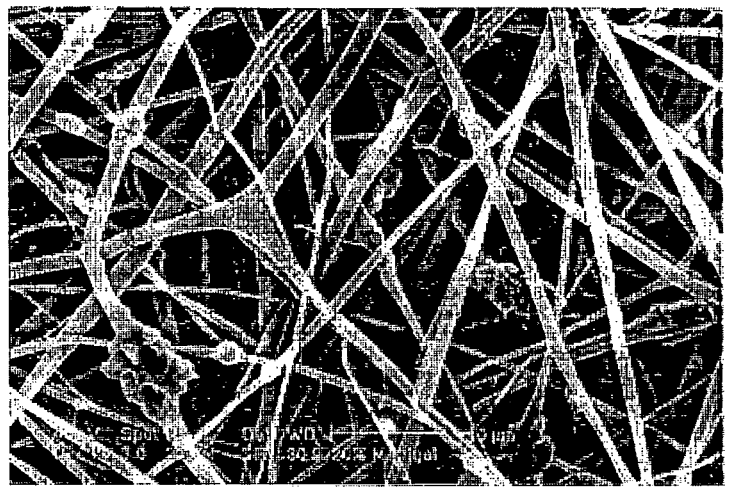
FIGS. 4A-4D are SEMs of electrospun MATRIGEL sheet (SEM-10222004) (raw fibers and cross-section are displayed).
Figure 4B:
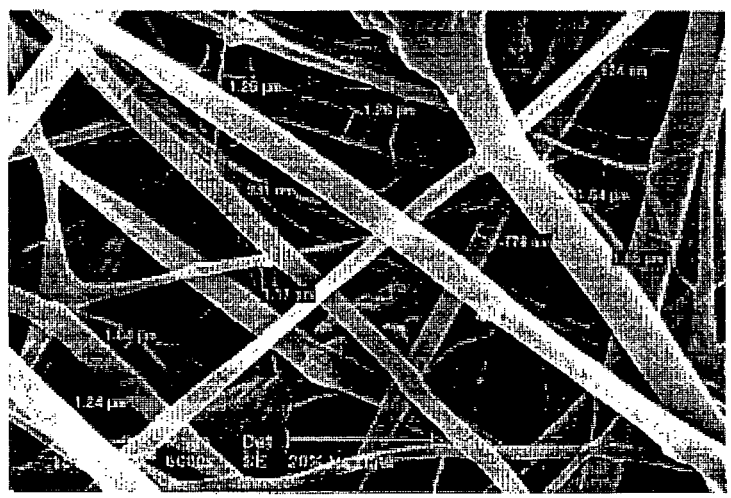
Figure 4C:
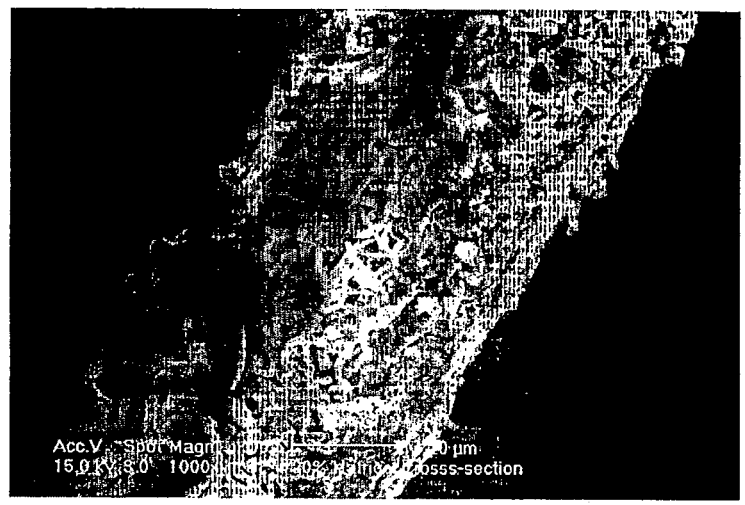
Figure 4D:
Figure 4E:
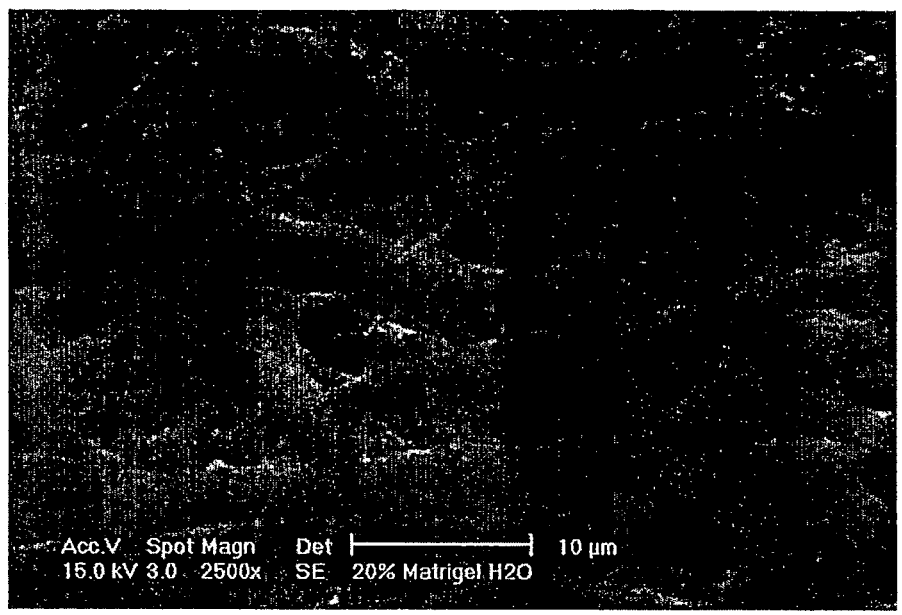
FIG. 4E is an SEM of electrospun MATRIGEL sheet (SEM-10222004): H2O treated.
Figure 4F:
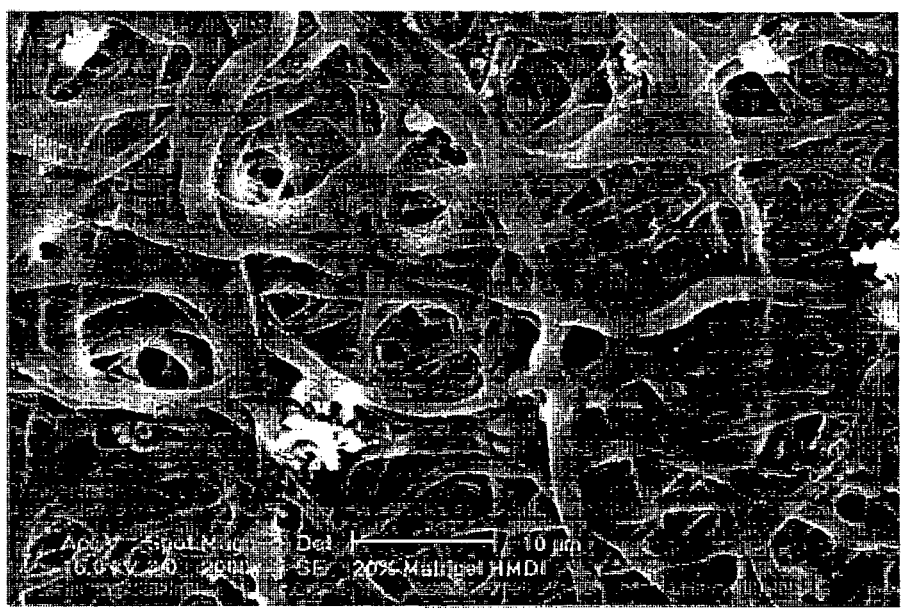
FIG. 4F is an SEM of electrospun MATRIGEL sheet (SEM-10222004): HMDI treated.
Figure 4G:
FIG. 4G is an SEM of electrospun MATRIGEL sheet (SEM-10222004): EDC treated.
Figure 4H:
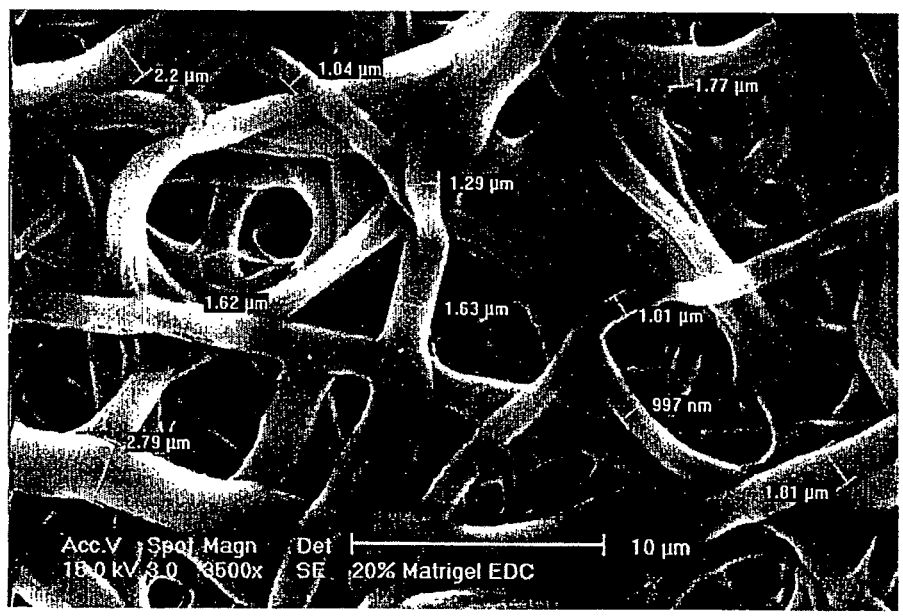
FIG. 4H is an SEM of electrospun MATRIGEL sheet (SEM-10222004)
Figure 5:
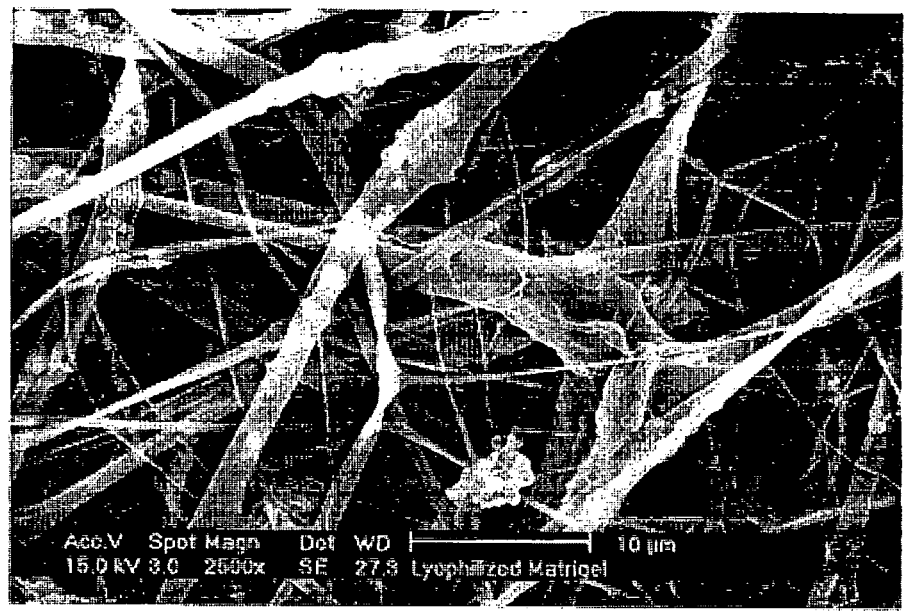
FIG. 5 is an SEM of electrospun MATRIGEL, (dialyzed by dd H2O instead of DMEM).
Figure 6A:
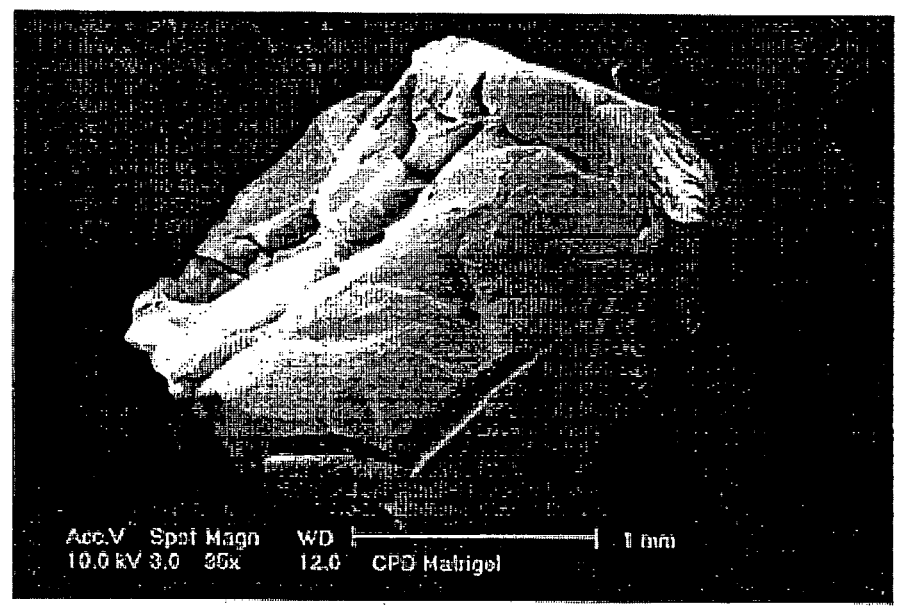
FIGS. 6A-6F are SEMs of CPD MATRIGEL scaffold made by the critical point drying method of the invention.
Figure 6B:
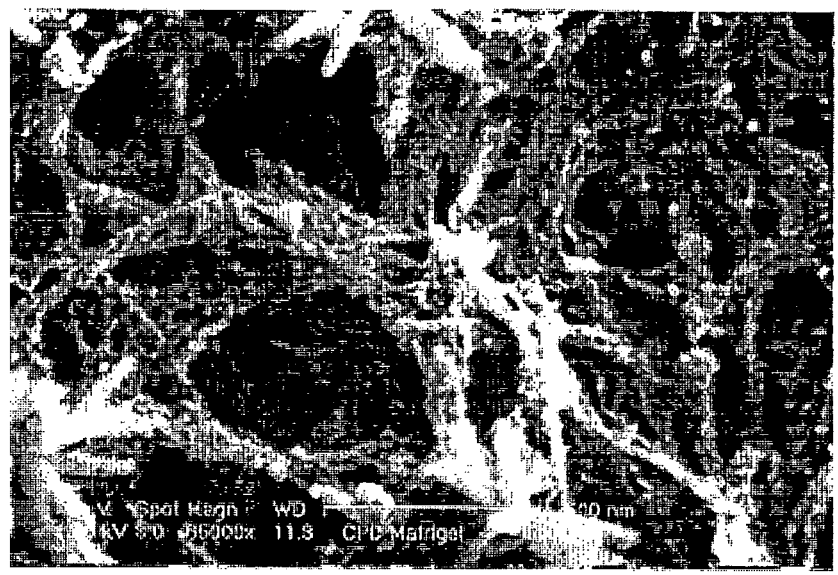
Figure 6C:
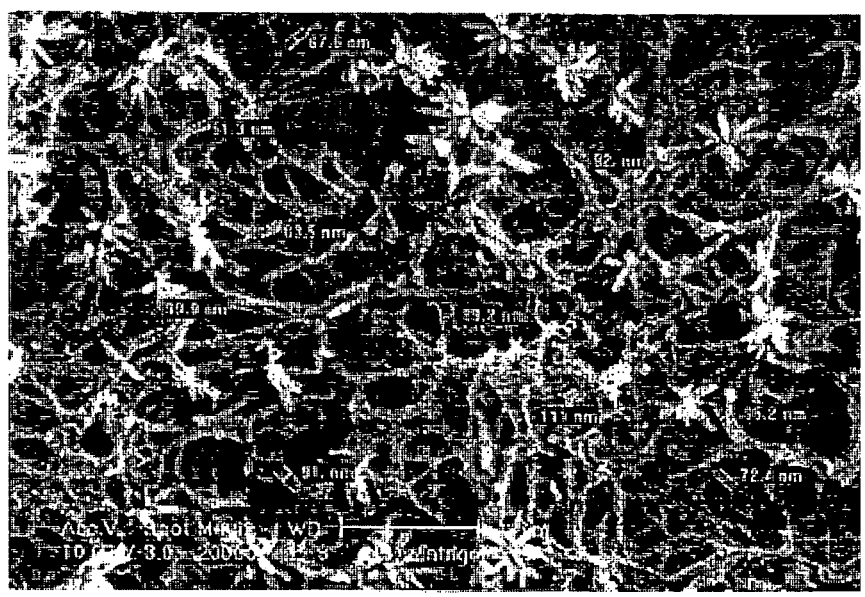
Figure 6D:
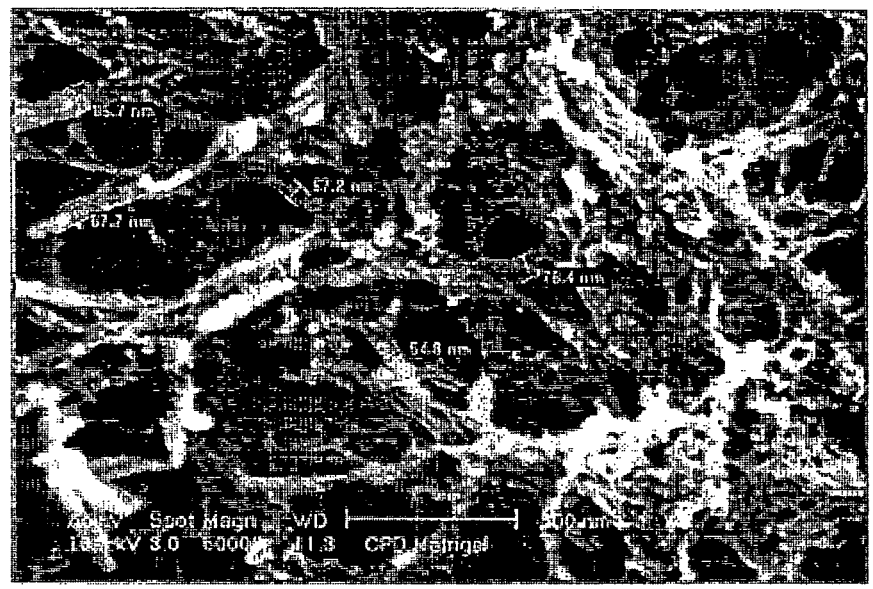
Figure 6E:
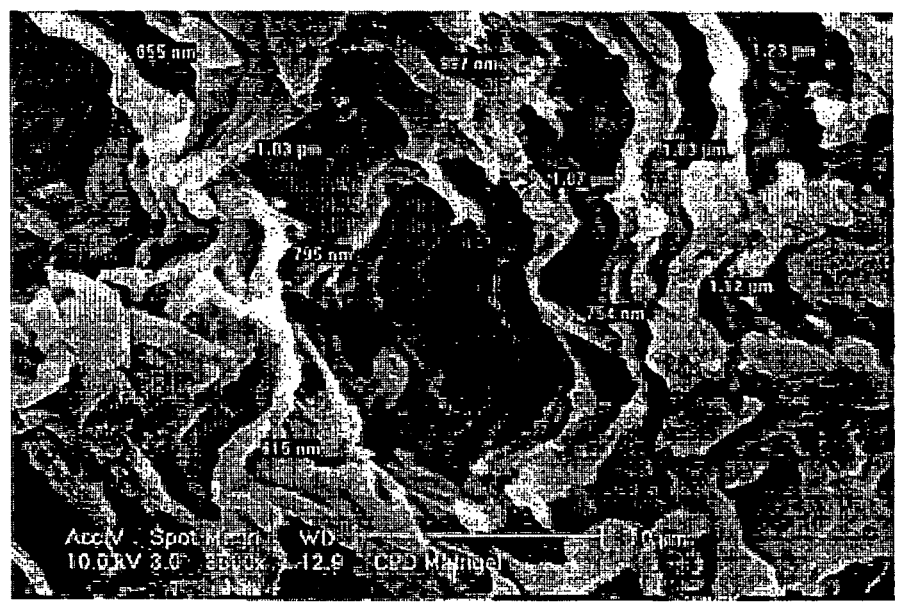
Figure 6F:
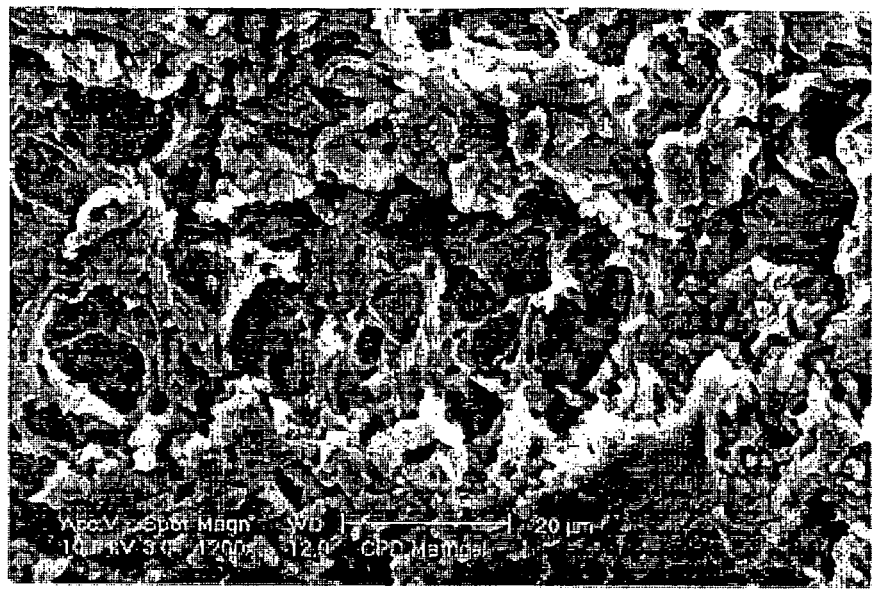
Figure 7A:
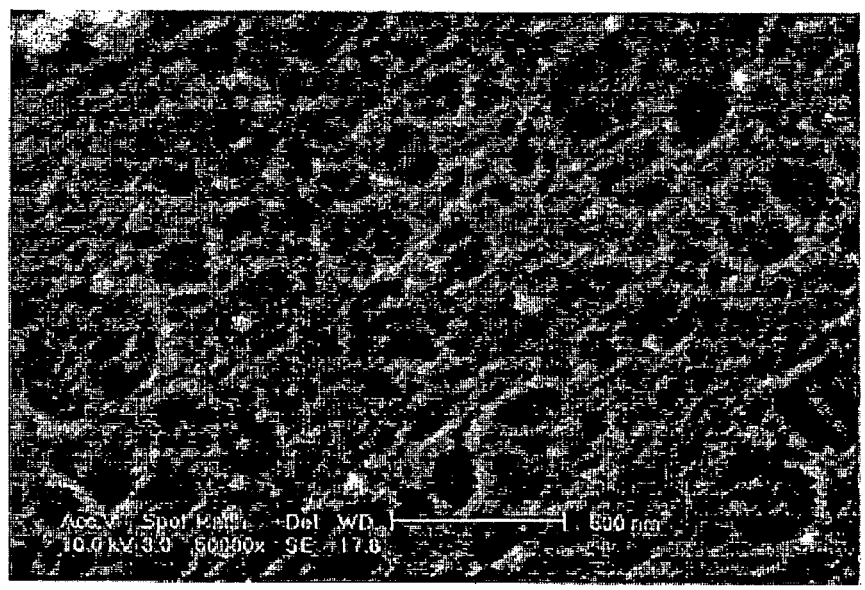
FIGS. 7A-7C are SEMs of CPD MATRIGEL scaffolds which display tubular fibrous structures with a diameter of 50-60 nanometers.
Figure 7B:
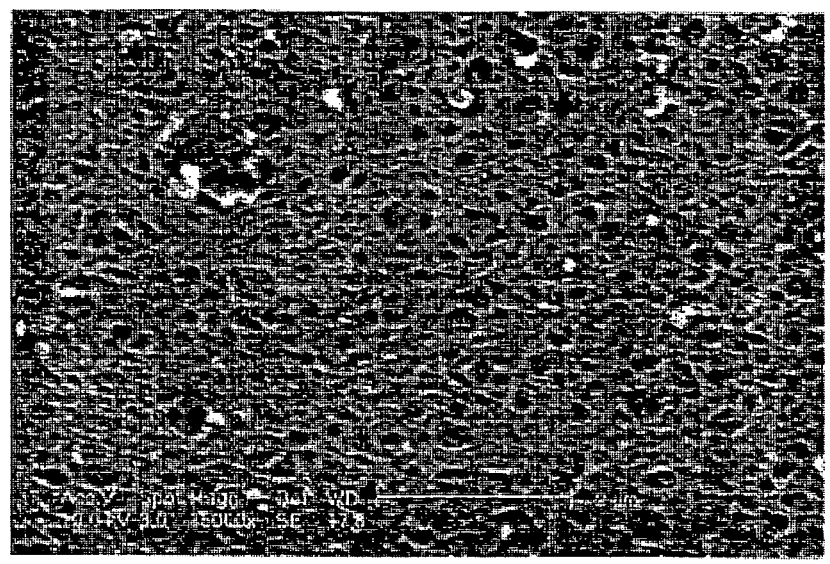
Figure 7C:
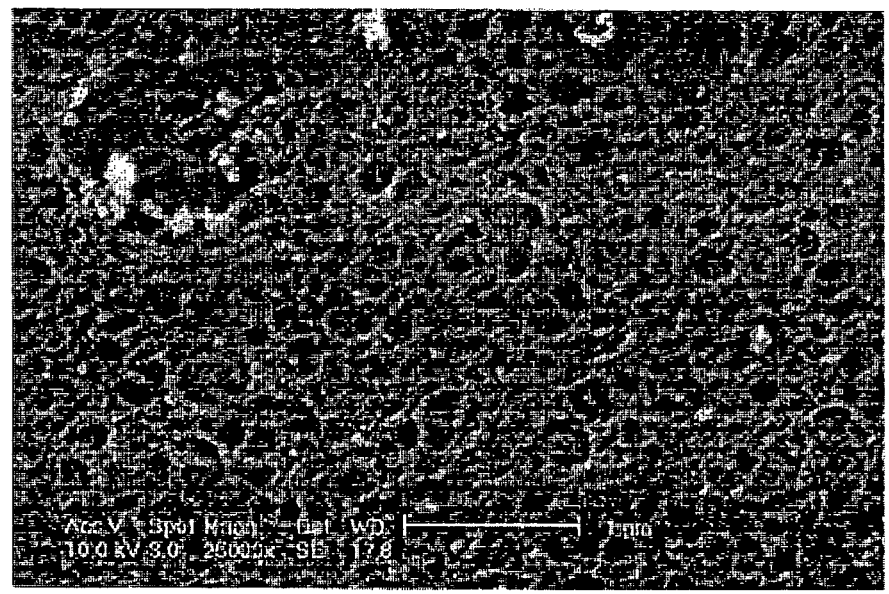
Figure 8B:
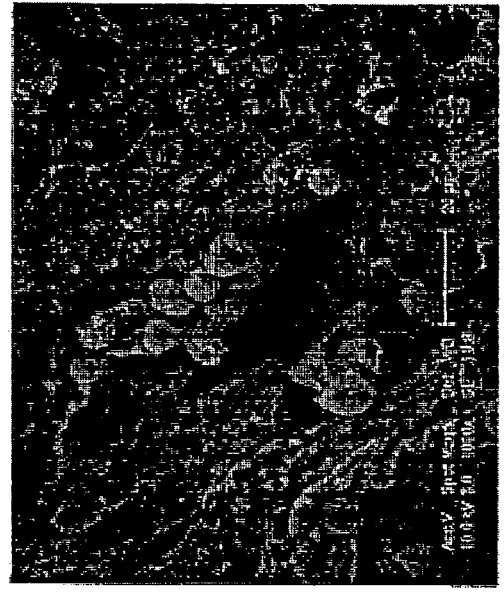
FIG. 8A-8C are SEMs of PC12 cells in FD MATRIGEL scaffolds made by the lyophilization (freeze-drying) method of the invention demonstrating that the cells are located in the pores and they are growing neurons.
Figure 8A:
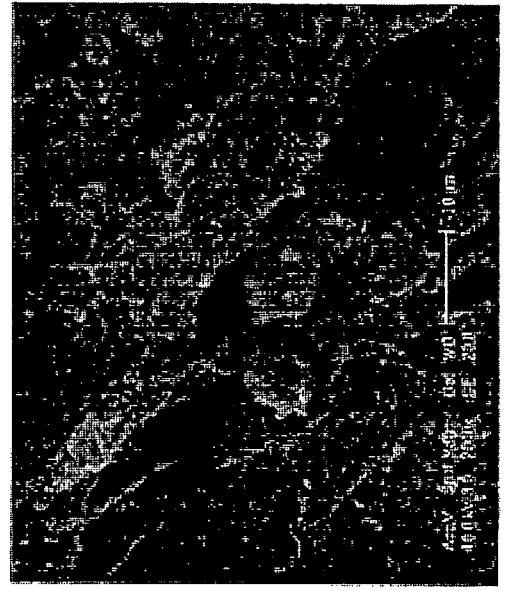
Figure 8C:

Electrospun Lyophilized Matrigel Scaffolds in Organic Solvent (FIGS. 1A-C, 2, 3A-3B, 4A-4H, and 5):
Solution Preparation:
 Thawed 25 ml MATRIGEL at 4° C. or use the extracted MATRIGEL directly after extraction.
 Freeze MATRIGEL in the liquid nitrogen fume for 15 minutes.
 Lyophilized (Freeze-dried) MATRIGEL in a lyophilizer for 2 days.
 Dissolved lyophilized Matrigel in 1,1,1,3,3,3 Hexafluoro-2-Propanol (HFP) and stirred in ~50° C. water-bath for overnight.
 The concentration is about 20% to about 30%.
 Waited for one day, and take the supernatant for electrospinning.
Electrospun Procedure:
 Electrical field: 10 kV
 Air distance from syringe tip to target collector: 10-15 cm
 Delivery rate of matrigel solution: 0.5 m/h-1 ml/h Example 4

Procedure of Measuring the Tensile Properties of Electrospun Fiber Mats:
Calculation of the density of PGE co-fibers, the electrospun MATRIGEL fiber mat:
 Assume the density of Matrigel sheet is 1.0 g/cc.
Methods:
 Microtensile test:
  Sample sheet length: 25 mm
  Sample sheet width: 5 mm
  Gauge length: 15 mm
  Density: 1.0 g/cc
  Sample weights (gm) and start/end points:

| Sample # | Material | Weight (gm) | Start point | End point |
|---|---|---|---|---|
| 0-1 | MATRIGEL | 0.0037 | 8 | 1513 |
| 0-2 | obtained as | 0.0036 | 35 | 2537 |

| Sample # | Material | Weight (gm) | Start point | End point |
|---|---|---|---|---|
| 0-3 | described in | 0.0030 | 24 | 1700 |
| 0-4 | EXAMPLE 2 | 0.0036 | 31 | 1977 |
| 0-5 | | 0.0039 | 67 | 2169 |

Example 5

Figure 14:
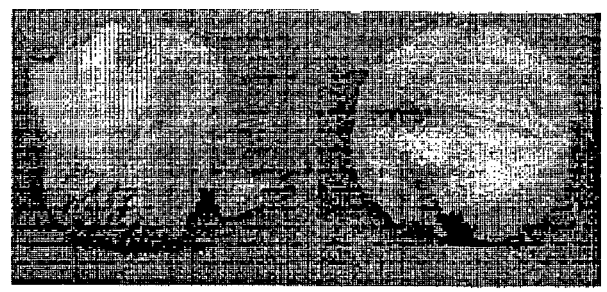
FIG. 14 demonstrates FD MATRIGEL scaffolds—dry.
Figure 15A:
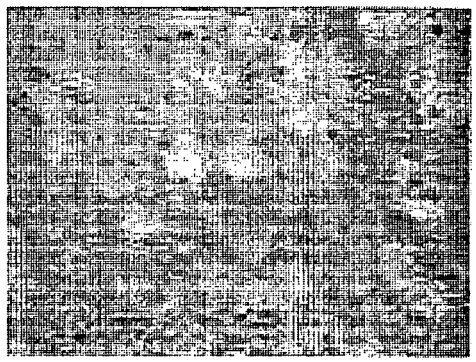
FIG. 15A demonstrates control MATRIGEL scaffolds without PC12 cells
Figure 15B:
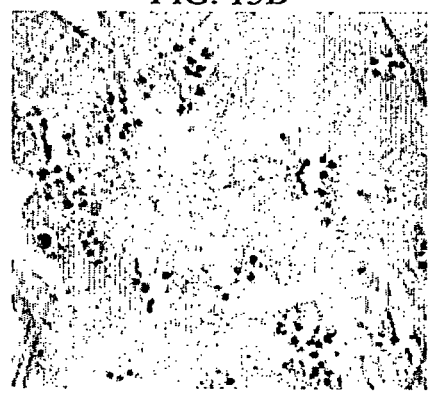
FIGS. 15B-15C are SEMs of MATRIGEL constructs with PC12 cells
Figure 15C:

Crosslinking Procedure for Electrospun/FD/CPD Scaffolds:
 EDC (1-Ethyl-3-[3-dimethylaminopropyl]carbodiimide Hydrochloride) solution:
  18 ml Acetone/Ethanol
  2 ml dd $H_2O$
  a pinch of EDC (25 mg)
Soaked in EDC solution for 1-2 hrs, rinsed by 1×PBS or dd H2O or DMEM w/ ABAM. See FIGS. 14 and 15A-C.

Example 6

Electrospun Lyophilized Matrigel Scaffolds in Aqueous Solution:
Solution Preparation:
  Thawed 25 ml MATRIGEL at 4° C. or use the extracted MATRIGEL directly after extraction.
  Dissolved extract MATRIGEL in 17.4N acetic acid or 80%-50% acetic acid with 20%-50% ethanol and stirred in ~50° C. water-bath overnight.
  The concentration is about 20% to about 30%.
  Waited for one day, and take the supernatant for electrospinning.
Electrospun Procedure:
  Electrical field: 10 kV
  Air distance from syringe tip to target collector: 10-15 cm
  Delivery rate of MATRIGEL solution: 0.5 m/h-1 ml/h Example 7

Figure 13A:
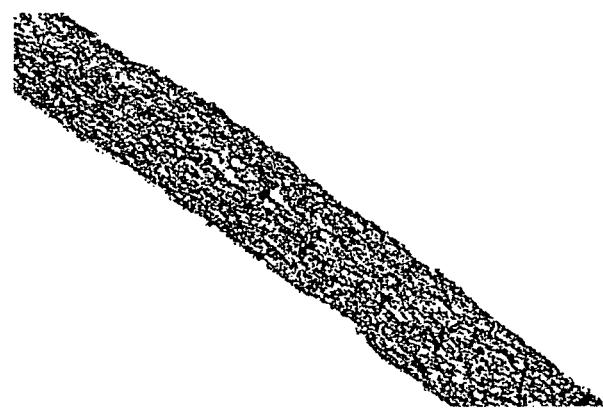
FIG. 13A-13B are pictures demonstrating histology section of FD MATRIGEL scaffolds for control MATRIGEL scaffold samples without H9C2 cells at 10×, 40× magnification respectively.
Figure 13B:
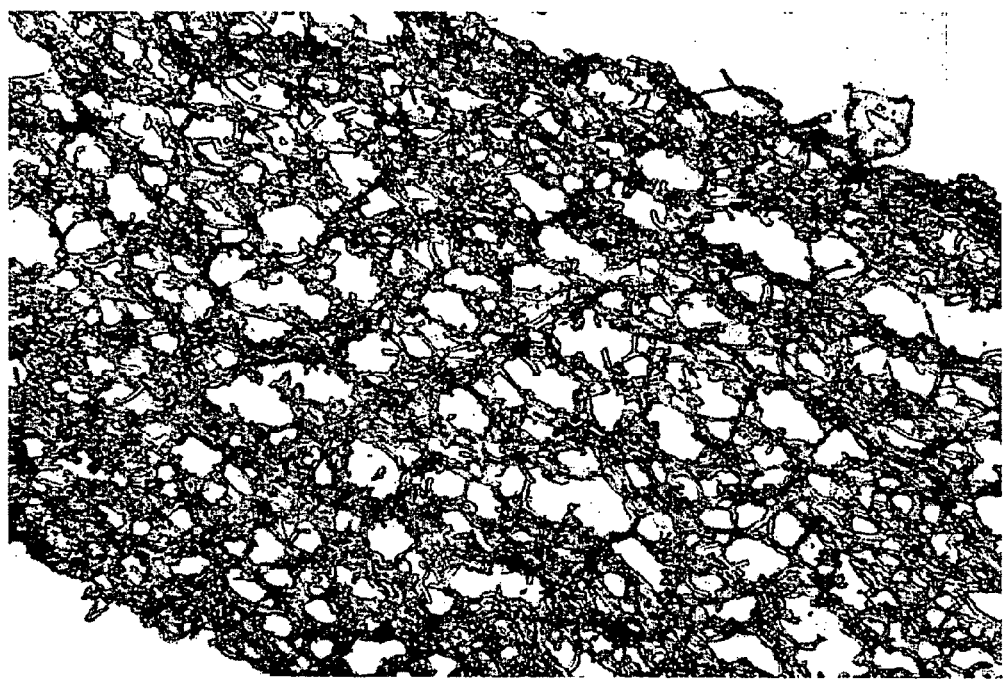
Figure 13C:
FIG. 13C-13D are pictures demonstrating histology section of FD MATRIGEL constructs with H9C2 cells at 10×, 40× magnification respectively.
Figure 13D:
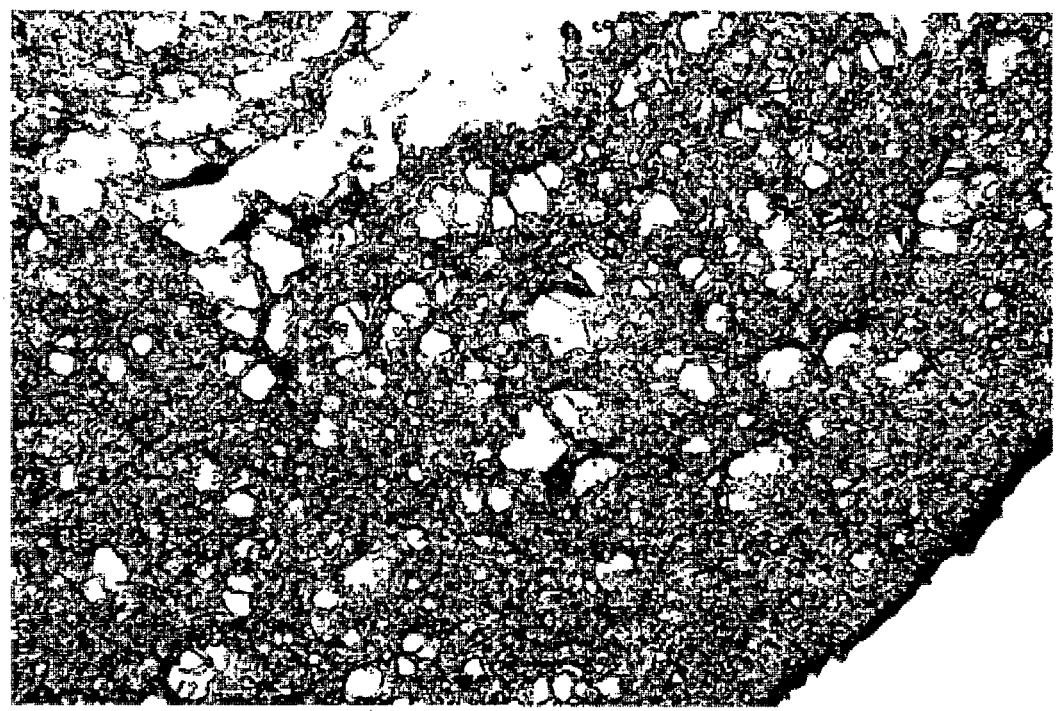
Figure 17A:
FIGS. 17A-17C are SEMs of histology sections of CPD MATRIGEL scaffolds.
Figure 17B:
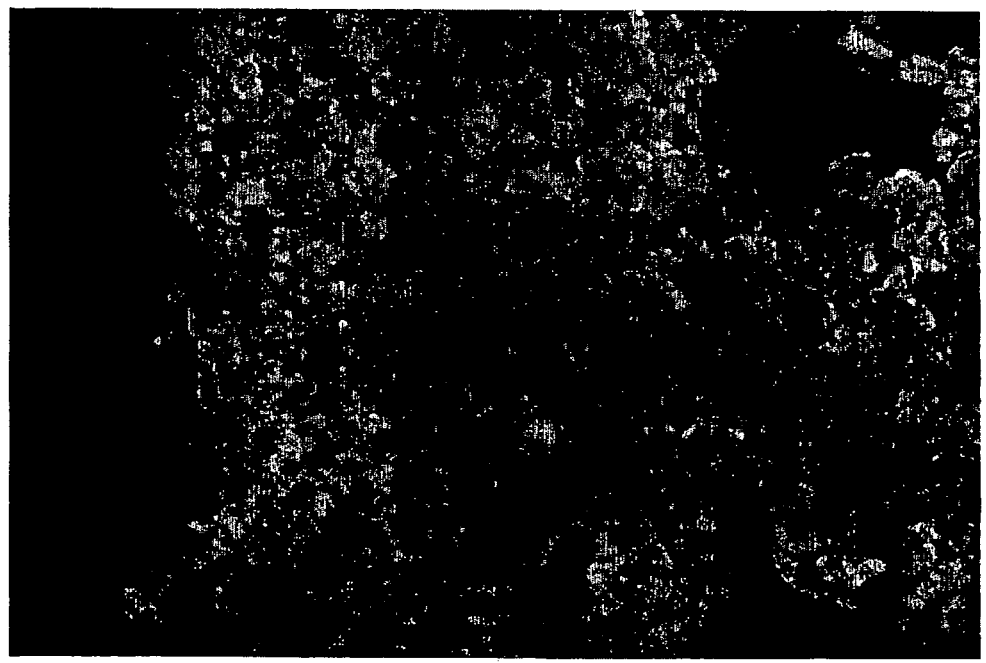
Figure 17C:
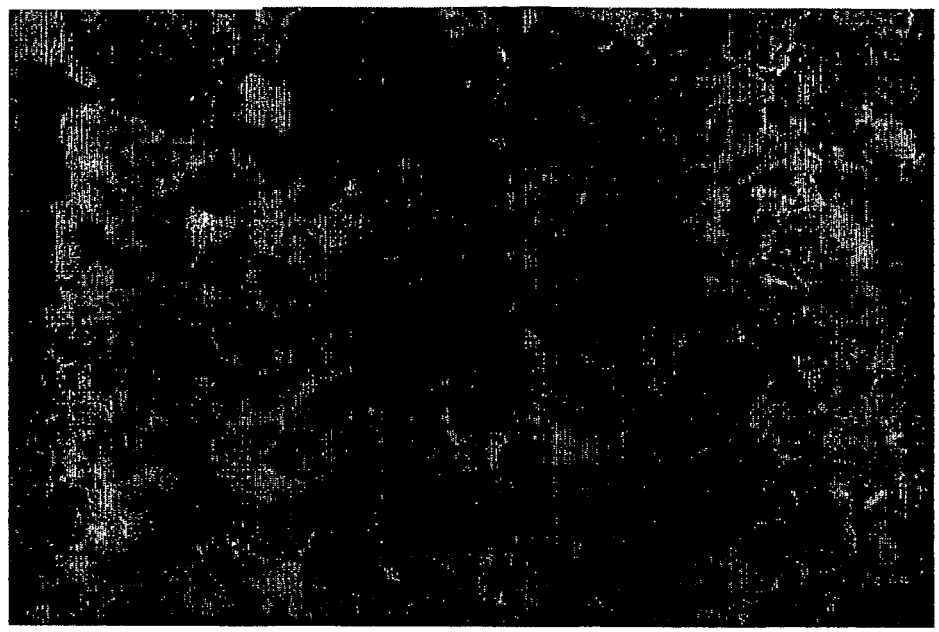
Figure 17D:
FIG. 17D is a SEM picture of Control CPD MATRIGEL Scaffolds without PC12 cells (Dry).
Figure 18:
FIGS. 18A-18B are SEMs of histology section (12 mm) of CPD/PC12 scaffolds, The CPD is populated with PC12 cells, with individual distribution. ×100
Figure 18B:
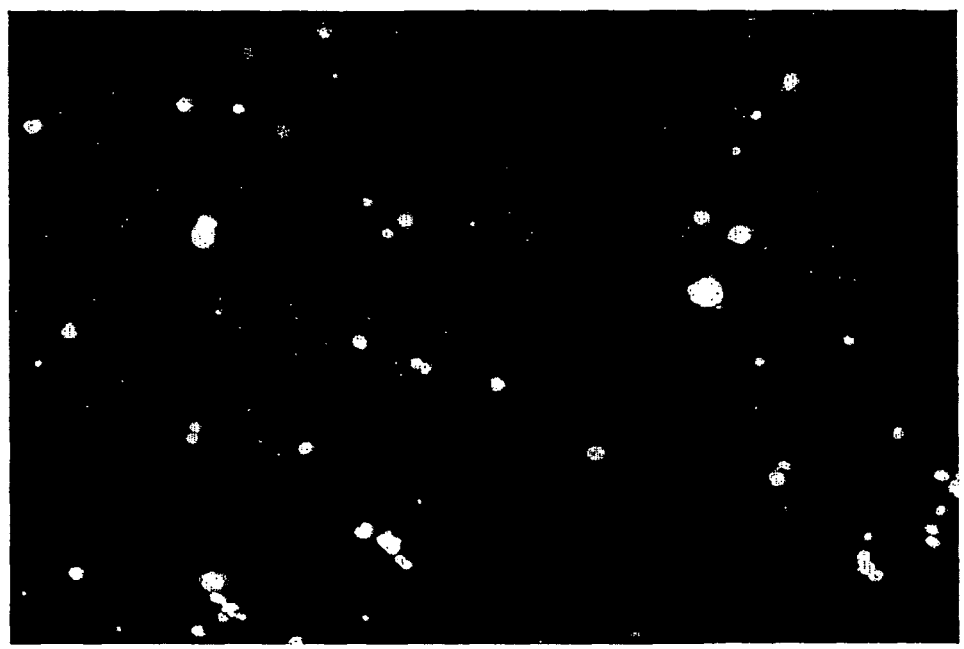

Histological analysis of samples (FIGS. 13A-13D, 17A-D).
It was observed that cell nuclei were stained by Hematoxylin in blue color and MATRIGEL scaffolds and cytoplasm of cells were staining by Eosin in red on histological slides. Also, cells attached on the scaffolds were observed.
  The following protocol was followed:
  Fix the cell/scaffold constructs:
  Wash cell with pH 7.4 1×PBS (either w/ Ca2+ or w/o Ca2+) for 2-3 times;
  Fix w/ Formaldefresh (commercial, ready to use) for 1-2 hrs at RT & overnight at 4 C in fridge;
  Wash w/ pH 7.4 1×PBS 2-3 times, 1-2 min each time;
  Store in 1×PBS or process for histology.
  Embedding scaffolds in Freezing medium:
  Embedding scaffolds in freezing medium for 1 hr at RT;
  Freeze in −80 C for more than 2 hrs.
  Coating microscope glass slides with poly-L-lysine
  Soaked slides in 0.1% (w/v) poly-L-lysine coating solution for 30-60 min;
  Rinsed in dd H2O and dried up.
  Cutting sections with 10 μm thickness and wait for drying up.
  H&E staining:
  70% Ethanol: 2-5 min; (remove freezing medium)
  Hematoxylin: 30-50 sec; (stain nuclei)
  Tap water for more blue color: 2-3 min;
  Eosin: 2 min;
  70% Ethanol: 2-5 min.
  BBZ staining (1 μg/ml in 1×PBS) for samples without H&E stain.

Example 8

Figure 9:
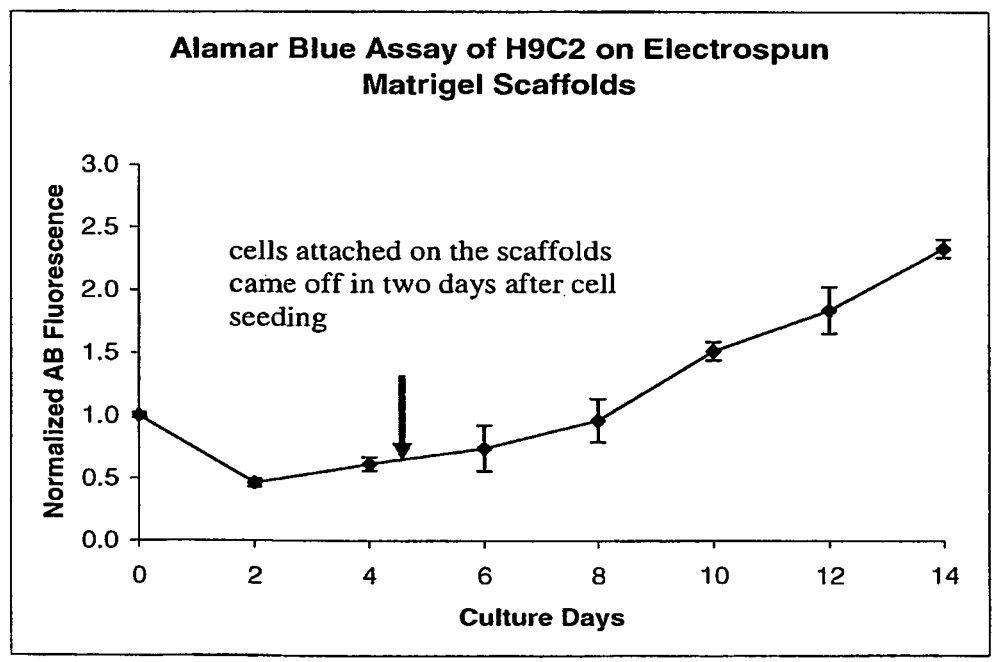
FIG. 9 is a graph demonstrating Alamar Blue Assay of H9C2 on electrospun MATRIGEL scaffolds.
Figure 10:
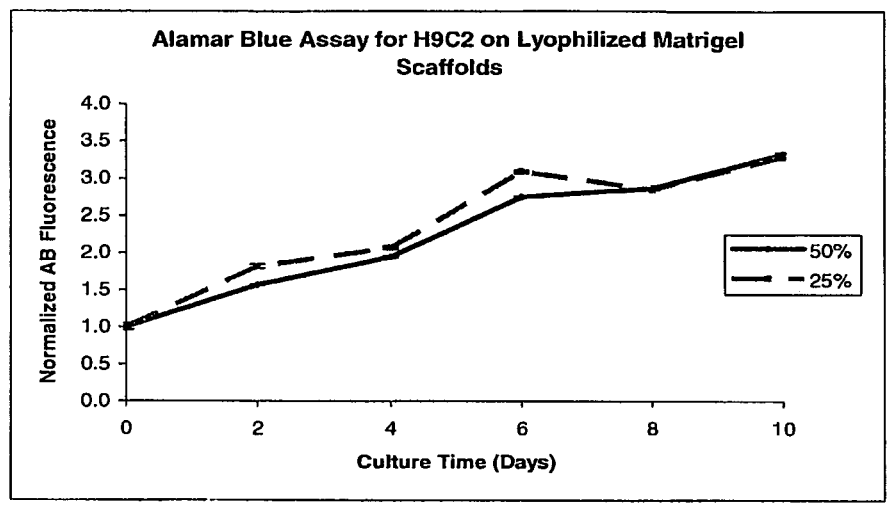
FIG. 10 is a graph demonstrating Alamar Blue Assay of H9C2 on lyophilized MATRIGEL scaffolds.
Figure 11:
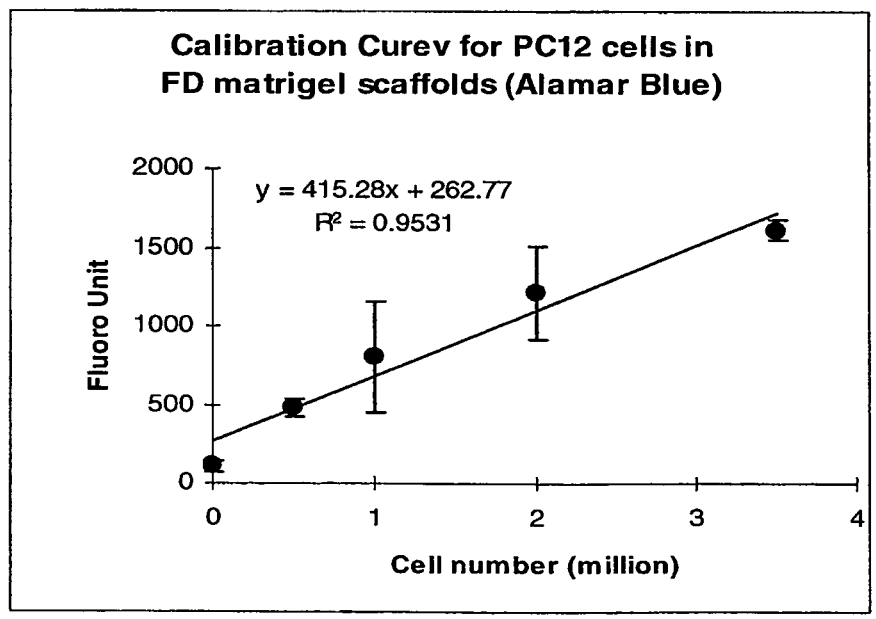
FIG. 11 demonstrates Calibration Curves for PC12 cells in FD MATRIGEL scaffolds (Alamar Blue)
Figure 12:
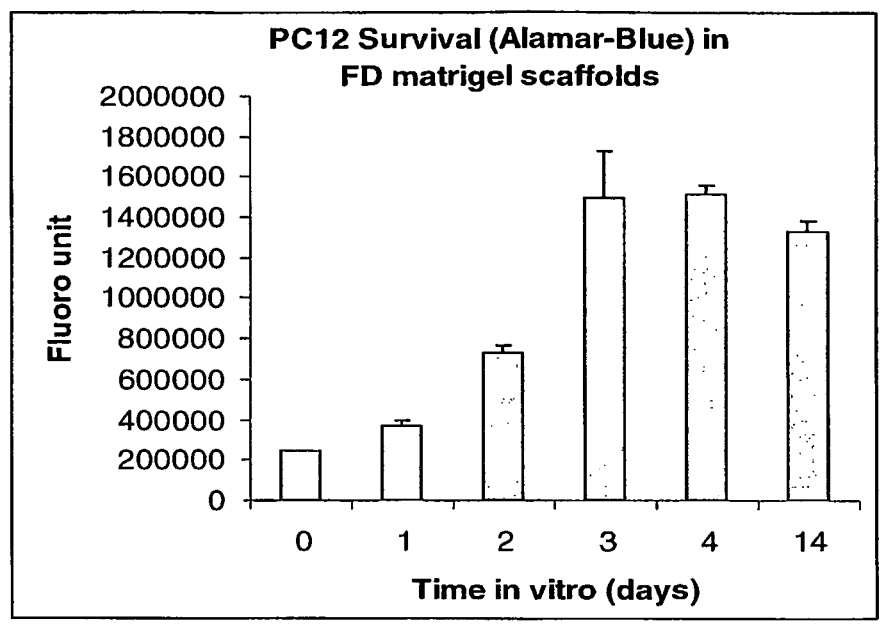
FIG. 12 is a graph demonstrating PC12 survival (Alamar-Blue) in FD MATRIGEL scaffolds.

Cell Culture and Measurement on Scaffolds:
A. Culturing Cells on Lyophilized Matrigel Scaffolds:
1. Scaffolds Preparation and Cell Seeding
  Lyophilize MATRIGEL for 2 days.
  Scaffolds were crosslinked with 0.5% (w/v) EDC in acetone or ethanol.
  Sterilize scaffolds in 10% ABAM in 1×PBS for overnight.
  Adding cells to scaffolds with cell number of 2 million.
  Shake the scaffolds and cell suspension on the orbital shaker for overnight—around 12 hrs.
  Measure Alamar Blue (AB) as the data of Day 0.
2. Alamar Blue Assay (FIGS. 9-12):
  5% AB in High-glucose complete DMEM.
  Transfer the scaffold-cell constructs to new wells for AB incubation 4 hrs.

Example 9

Figure 16A:
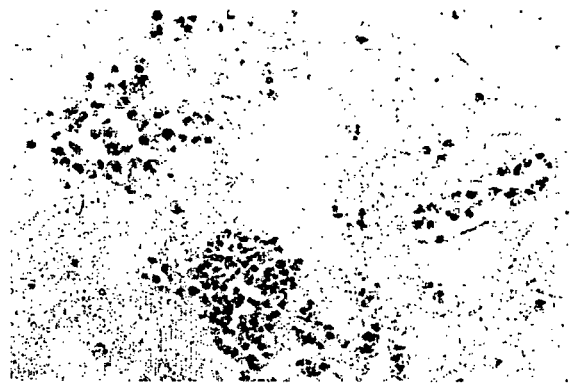
FIGS. 16A-16B are SEMs of Haematoxylin-Eosin (H&E) stained section (12 mm) of FD/PC12 scaffolds, 3 days after seeding shows that the FD scaffolds are populated with PC12 cells, with clustered aggregates in the pores (×100).
Figure 16B:
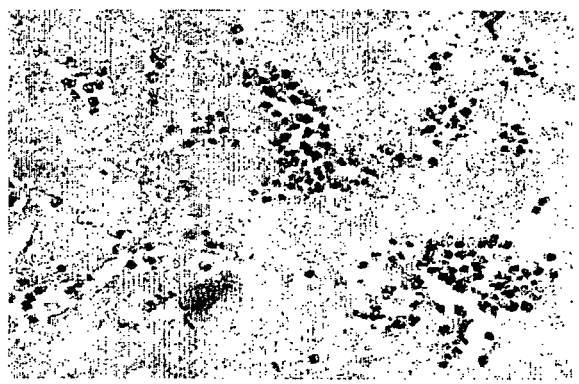
Figure 19:
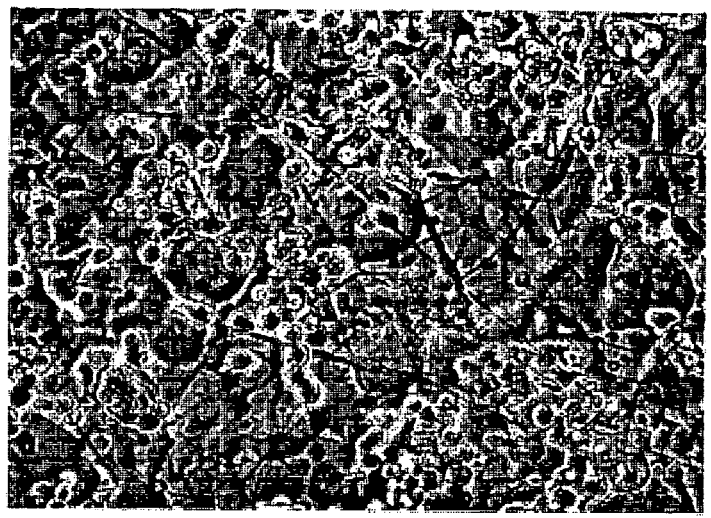
FIG. 19 is a phase contrast micrograph of PC12 Cells 48 hours after seeding on electrospinning MATRIGEL. ×200.
Figure 20A:
FIGS. 20A-20C are SEMs of PC12 cells on electrospunned MATRIGEL scaffold, 5 days post seeding wherein generating neurons is observed, wherein magnification is 20 um, 5 um and 10 um respectively.
Figure 20B:
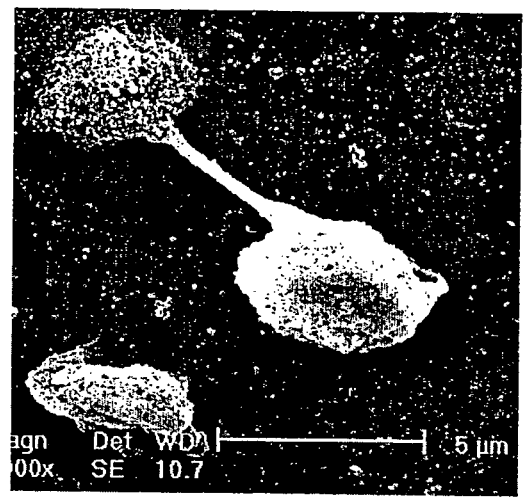
Figure 20C:
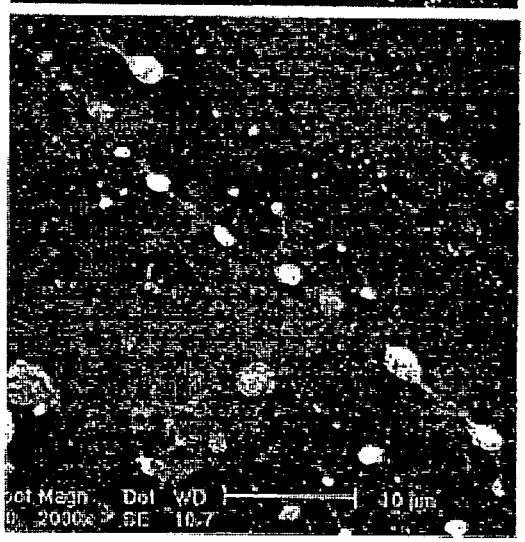

PC12 cells were grown on scaffolds demonstrating growing neurons (FIGS. 16A-16B, 19, and 20A-C.

Example 10

CPD Processed Unfractionated Extracellular Matrix Extract
Hydrogel samples of collagen, fibrin and MATRIGEL were fixed with 2.5% glutaraldehyde for 1 hour at room temperature and then left overnight at 4° C. The samples were washed with cacodylate buffer, and dehydrated in 15%, 30%, 50%, 70%, 85%, 95%, and 100% (twice) graded ethanol for 10 min each followed by drying in a critical point dryer (CPD, SPI CPD 7501, West Chester Pa.). SEM micrographs of CPD processed fibers showed that their diameters were less than 100 nm, very close to the native ECM.

Example 11

A method to generate aligned electrospun fibers:
  Electrical field: 10 kV
  Air distance from syringe tip to target collector: 10-15 cm
  Delivery rate of lyophilized unfractionated extracellular matrix extract solution: 0.5 m/h-1 ml/h
  The aligned fibers are collected on the mandrel with rotating speed of 5000 rpm.

Example 12

Future study on matrigel scaffolds with neuronal cells in vivo for spinal cord injury application.
Lineage-restricted neural precursors survive, migrate, and differentiate following transplantation into the injured adult spinal cord (as described in A. C. Lepore, I. Fischer T Department of Neurobiology and Anatomy, 2900 Queen Lane, Drexel University College of Medicine, Philadelphia, Pa. 19129, USA, Experimental Neurology 194 (2005) 230-242).
Adult spinal cord injury and transplants Lateral funiculus injuries will be created at the cervical 4 spinal cord level. Adult female Sprague-Dawley rats (approximately 250 g) will be receiving intraperitoneal injections of anesthetic cocktail. The back musculature will be excised, and a laminectomy will performed at the cervical 3/4 level. The dura will be incised above the dorsal root entry zone. Microscissor cuts will be created at the rostral and caudal extents of the injury. Aspiration will be used to selectively ablate only the lateral white matter tracts, as well as a minimal portion of the dorsal and ventral gray matter. The dorsal columns and central canal will be unaffected. Once hemostasis the scaffolds with the cells will be implanted into the injury cavity using either a 10-AL Hamilton Gastight syringe (Hamilton; Reno, Nev.) or forceps, respectively. Dura will be closed with 9-0 suture; muscle will be re-apposed; skin will be closed with wound clips. Animals will be receiving Bupranorphin and methylprednisolone (Pharmacia and Upjohn; Kalamazoo, Mich.) postoperatively. Animals will be immunosuppressed by subcutaneous administration of cyclosporine daily beginning 3 days before grafting and continuously until sacrifice.

Tissue processing: Animals will be sacrificed at various time points (4 days, 3 and 5 weeks) following transplantation by transcardial perfusion with 0.9% saline, followed by ice-cold 4% paraformaldehyde (Fisher Scientific; Pittsburgh, Pa.). Spinal cords will be removed from the animals. The tissue will be embedded in OCT, fast frozen with dry ice, and stored until processed.

While the invention has been described in detail and with reference to specific examples thereof, it will be apparent to one skilled in the art that various changes and modifications can be made therein without departing from the spirit and scope thereof.

REFERENCES

Sheu M T, Huang J C, Yeh G C, Ho H O. Characterization of collagen gel solutions and collagen matrices for cell culture. Biomaterials. 2001 July; 22(13):1713-9.

Long J L, Tranquillo R T. Elastic fiber production in cardiovascular tissue-equivalents. Matrix Biol. 2003 June; 22(4):339-50.

Yang F, Murugan R, Wang S, Ramakrishna S. Electrospinning of nano/micro scale poly(L-lactic acid) aligned fibers and their potential in neural tissue engineering. Biomaterials. 2005 May; 26(15):2603-10.

Xu C, Inai R, Kotaki M, Ramakrishna S. Electrospun nanofiber fabrication as synthetic extracellular matrix and its potential for vascular tissue engineering. Tissue Eng. 2004 July-August; 10(7-8):1160-8.

Shin M, Ishii O, Sueda T, Vacanti J P. Contractile cardiac grafts using a novel nanofibrous mesh. Biomaterials. 2004 August; 25(17):3717-23.

Boland E D, Matthews J A, Pawlowski K J, Simpson D G, Wnek G E, Bowlin G L. Electrospinning collagen and elastin: preliminary vascular tissue engineering. Front Biosci. 2004 May 1; 9:1422-32.

Willits R K, Skornia S L. Effect of collagen gel stiffness on neurite extension. J Biomater Sci Polym Ed. 2004; 15(12):1521-31.

Combelles C M, Fissore R A, Albertini D F, Racowsky C. In vitro maturation of human oocytes and cumulus cells using a co-culture three-dimensional collagen gel system. Hum Reprod. 2005 Feb. 3; [Epub ahead of print]

U.S. Pat. No. 6,682,760;

U.S. Pat. No. 6,753,454

U.S. Pat. No. 6,695,992

What is claimed is:

1. A method of making a biologically active three-dimensional scaffold capable of supporting growth and differentiation of a cell, the method comprising:
   providing an unfractionated extracellular matrix extract from a mammalian tissue in a form selected from the group consisting of a powder, a solution, a hydrogel and a suspension;
   placing the unfractionated extracellular matrix extract in a mold;
   freezing the unfractionated extra cellular matrix extract at 0° C. or below at a controlled freezing rate of less than about 1° C./min;
   freeze-drying the unfractionated extra cellular matrix extract by subjecting the unfractionated extracellular matrix extract to a temperature between about −130° C. and about −80° C. for a time sufficient to remove at least 90% of a liquid from the unfractionated extracellular matrix extract and thereby obtaining a lyophilized unfractionated extracellular matrix extract; and
   optionally crosslinking the lyophilized unfractionated extracellular matrix extract by contacting with a crosslinker and thereby providing the biologically active three-dimensional scaffold having porous morphology.

2. The method of claim 1, wherein the unfractionated extracellular matrix extract is provided in an organic solvent.

3. The method of claim 1, wherein the unfractionated extracellular matrix extract is provided in an aqueous medium.

4. The method of claim 1 further comprising crosslinking the lyophilized unfractionated extracellular matrix extract by contacting with a crosslinker.

* * * * *